(12) United States Patent
Khanale et al.

(10) Patent No.: US 10,407,686 B2
(45) Date of Patent: Sep. 10, 2019

(54) PLANT PROMOTER FROM COTTON AND USES THEREOF

(71) Applicant: MAHARASHTRA HYBRID SEEDS COMPANY LIMITED (MAHYCO), New Delhi (IN)

(72) Inventors: Vaishali Praveen Khanale, Aurangabad (IN); Anjanabha Bhattacharya, Kolkata (IN); Anindya Bandyopadhyay, Metro Manila (PH); Bharat Char, Maharashtra (IN)

(73) Assignee: MAHARASHTRA HYBRID SEEDS COMPANY LIMITED (MAHYCO), New Delhi (IN)

( * ) Notice: Subject to any disclaimer, the term of this patent is extended or adjusted under 35 U.S.C. 154(b) by 26 days.

(21) Appl. No.: 15/516,617

(22) PCT Filed: Mar. 4, 2016

(86) PCT No.: PCT/IN2016/050078
§ 371 (c)(1),
(2) Date: Apr. 3, 2017

(87) PCT Pub. No.: WO2016/139682
PCT Pub. Date: Sep. 9, 2016

(65) Prior Publication Data
US 2018/0273969 A1    Sep. 27, 2018

(30) Foreign Application Priority Data
Mar. 5, 2015 (IN) .............................. 627/DEL/2015

(51) Int. Cl.
*C12N 15/82* (2006.01)

(52) U.S. Cl.
CPC ..... *C12N 15/8216* (2013.01); *C12N 15/8227* (2013.01); *C12N 15/8237* (2013.01); *C12N 15/8238* (2013.01)

(58) Field of Classification Search
None
See application file for complete search history.

(56) References Cited

U.S. PATENT DOCUMENTS 5,352,605 A * 10/1994 Fraley ................... C07K 14/61
435/320.1

FOREIGN PATENT DOCUMENTS

WO    WO 01/44457 A2 * 6/2001

OTHER PUBLICATIONS

Wahl et al., Meth Enzymol 152:399-407 (1987).*
Donald & Cashmore, EMBO J 9:1717-26 (1990).*
Dolferus et al., Plant Physiol 105:1075-87 (1994).*
Kim et al., Plant Mol Biol 24:105-17 (1994).*
Potenza et al., In Vitro Cell Dev Biol Plant 40:1-22 (2004).*
Saha et al., In Silico Biol 7(1):7-19 (2007).*
Dezar et al., Plant Sci 169:447-56 (2005).*
Priest et al., Curr Opin Plant Biol 12:643-49, 645 (2009).*
Fourgoux-Nicol et al., Plant Mol Biol 40:857-72 (1999).*
Wahl et al. (1987) Meth Enzymol 152:399-407.*
USPTO WD Training Materials (2008).*
GenBank Accession No. ALYE01014695.1, "Gossypium raimondii Chr11_contig_507, whole genome shotgun sequence," (72 pages) (Dec. 20, 2012).
Hsu et al., "Analysis of promoter activity of cotton lipid transfer protein gene LTP6 in transgenic tobacco plants," *Plant Science* 143:63-80 (1999).
Viana et al., "Isolation and functional characterization of a cotton ubiquitination-related promoter and 5'UTR that drives high levels of expression in root and flower tissues," *BMC Biotechnology* 11:115 (11 pages) (2011).

* cited by examiner

*Primary Examiner* — Russell T Boggs
(74) *Attorney, Agent, or Firm* — Seed IP Law Group LLP

(57) ABSTRACT

The present disclosure provides a cotton promoter, designated "p2", which exhibits promoter activity. Interestingly, the promoter is also influenced by water or salt stress. Deletion analysis reveals upstream elements/motifs in the promoter which influence promoter activity, and sequences that are potentially responsive to salt or water stress.

16 Claims, 10 Drawing Sheets

Specification includes a Sequence Listing.

p2Δ1-Exp.2-8B    p2Δ2-Exp.1-5A    p2-8A-15-9

PLANT PROMOTER FROM COTTON AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 630250_401USPC_SEQUENCE_LISTING.txt. The text file is 6.7 KB, was created on Mar. 30, 2017, and is being submitted electronically via EFS-Web.

FIELD OF INVENTION

The present disclosure relates to plant molecular biology and genetic engineering. In particular, the disclosure relates to isolation and characterization of an inducible promoter from cotton.

BACKGROUND OF THE INVENTION

Promoters contain specific DNA sequences and response elements that provide a secure initial binding site for RNA polymerase and for proteins called transcription factors that recruit RNA polymerase. These transcription factors have specific activator or repressor sequences of corresponding nucleotides that attach to specific promoters and regulate gene expression.

Promoters used in biotechnology are of different types according to the intended type of control of gene expression. An extensive number of plant promoters, are reported in the literature. These plant promoters act as useful tools for expressing proteins or peptides in transgenic plants or plant cells or alternatively for silencing genes or gene families. Promoters are generally grouped into following categories namely: constitutive promoters, inducible promoters, developmentally regulated promoters, and tissue specific promoters.

Constitutive promoters direct expression in virtually all the tissues and are largely independent of environmental and developmental factors. As their expression is normally not conditioned by endogenous factors, constitutive promoters are usually active across species and even across kingdoms.

Numerous promoters that function in plant cells are known in the art and are available for use in recombinant polynucleotides for expression of desired genes in transgenic plant cells.

U.S. Pat. No. 5,510,474 describes a maize ubiquitin promoter; U.S. Pat. No. 5,850,018 describes a maize ZMDJ1 promoter/leader sequence, and US 20110167518 describes a maize sark promoter.

Viral promoters capable of infecting plants are less preferred for the transformation of host plant species, as infection of the plants with the virus may cause silencing of the transgene (Seemanpillai et al., 2003, Mol Plant Microbe Interact. 16(5): 429-438; Al-KafFef al, 2000, Nat Biotechnol. 18: 995-9).

Currently commonly used constitutive promoter is the 35S promoters or enhanced 35S promoters (the "35S promoters") of the cauliflower mosaic virus (CaMV) of isolates CM 1841 (Gardner et al., 1981, Nucleic Acids Research 9, 2871-2887) CabbB-S (Franck et al, 1980, Cell 21, 285-294) and CabbB-JI (Hull and Howell, 1978, Virology 86, 482-493); the 35S promoter described by Odell et al (1985, Nature 313, 810-812).

WO2007069894 describes that the activity of the CaMV35S promoter in transgenic plants was sensitive to abiotic stress, especially heat stress caused when the transgenic plants were grown in the field in Spain.

There is a need for development of different constitutive plant promoters for gene stacking approaches, as the use of several identical promoters may result in gene silencing (Yang et al., 2005, Plant Mol Biol. 58: 351-366).

Isolation and functional characterization of a cotton ubiquitination-related promoter and 5'UTR that drives high levels of expression in root and flower tissues has already been described. uceA1.7 is a strong constitutive regulatory sequence composed of a promoter (uceApro2) and its 5'UTR is useful in genetic transformation of dicots, having high potential to drive high levels of transgene expression in crops, particularly for traits desirable in flower and root tissues (Viana et al., 2011, BMC Biotechnology, 11:115). Promoters from cotton specific to green tissues, flower buds-inflorescences (with lower activity in vegetative tissues), seed and fiber are disclosed in the prior arts It is desirable from a regulatory point of view to use promoters derived from plants in the generation of transgenic plants. Therefore, new constitutive promoters of plant origin are required, which regulate transgene expression positively in response to adverse environmental stress. This will directly help in the field of plant biotechnology to improve crop yields for assurance of global food security.

SUMMARY OF THE INVENTION

In an aspect of the present disclosure, there is provided a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1.

In an aspect of the present disclosure, there is provided a DNA construct comprising a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, wherein said DNA fragment is operably linked to a heterologous nucleic acid sequence.

In an aspect of the present disclosure, there is provided a DNA vector comprising a DNA construct, said DNA construct comprising a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, wherein said DNA fragment is operably linked to a heterologous nucleic acid sequence.

In an aspect of the present disclosure, there is provided a recombinant host cell comprising a DNA construct comprising a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, wherein said DNA fragment is operably linked to a heterologous nucleic acid sequence, wherein said host cell is of bacterial, fungal, or plant origin.

In an aspect of the present disclosure, there is provided a recombinant host cell comprising a DNA vector comprising a DNA construct, said DNA construct comprising a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, wherein said DNA fragment is operably linked to a heterologous nucleic acid sequence, wherein said host cell is of bacterial, or fungal origin.

In an aspect of the present disclosure, there is provided a transgenic plant or part thereof, including seeds, comprising within its genome, a DNA construct comprising a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, wherein said DNA fragment is operably linked to a heterologous nucleic acid sequence.

In an aspect of the present disclosure, there is provided a transgenic plant or parts thereof, including seeds, capable of expression of a gene of interest driven heterologously by a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1.

In an aspect of the present disclosure, there is provided a method of generating a transgenic plant comprising within its genome, a DNA construct comprising a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, wherein said DNA fragment is operably linked to a heterologous nucleic acid sequence; or capable of expression of a gene of interest driven heterologously by a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, said method comprising: (a) obtaining plant cell(s); (b) obtaining a DNA construct comprising a promoter capable of driving or regulating expression of an operably linked gene of interest in a constitutive or stress inducible manner, comprising: (i) a DNA fragment as set forth in SEQ ID NO: 1 or complement thereof; or (ii) a DNA fragment having at least 90% sequence identity to any contiguous stretch of DNA sequence as set forth in SEQ ID NO: 1; or (iii) a DNA fragment capable of hybridizing under stringent conditions with any contiguous stretch of DNA sequence as set in SEQ ID NO: 1, wherein said DNA fragment is operably linked to a heterologous nucleic acid sequence; or a recombinant host cell comprising a DNA vector comprising a DNA construct, said DNA construct comprising a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, wherein said DNA fragment is operably linked to a heterologous nucleic acid sequence, wherein said host cell is of bacterial, or fungal origin; (c) transforming said plant cell(s) with said DNA construct, or said recombinant host cell to obtain transformed plant cell(s); and (d) selecting transformed plant cell(s) expressing said gene of interest.

In an aspect of the present disclosure, there is provided a method of heterologous expression of a gene of interest driven by a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, said method comprising: (a) obtaining plant cell(s); (b) obtaining a DNA construct comprising a promoter capable of driving or regulating expression of an operably linked gene of interest in a constitutive or stress inducible manner, comprising: (i) a DNA fragment as set forth in SEQ ID NO: 1 or complement thereof; or (ii) a DNA fragment having at least 90% sequence identity to any contiguous stretch of DNA sequence as set forth in SEQ ID NO: 1; or (iii) a DNA fragment capable of hybridizing under stringent conditions with any contiguous stretch of DNA sequence as set in SEQ ID NO: 1, wherein said DNA fragment is operably linked to a heterologous nucleic acid sequence; or a recombinant host cell comprising a DNA vector comprising a DNA construct, said DNA construct comprising a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, wherein said DNA fragment is operably linked to a heterologous nucleic acid sequence, wherein said host cell is of bacterial, or fungal origin; (b) transforming plant cell(s) with said DNA construct, or said recombinant host cell to obtain transformed plant cell(s); and (c) selecting transformed plant cell(s) heterologously expressing said gene of interest.

BRIEF DESCRIPTION OF THE ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

Figure 5A:
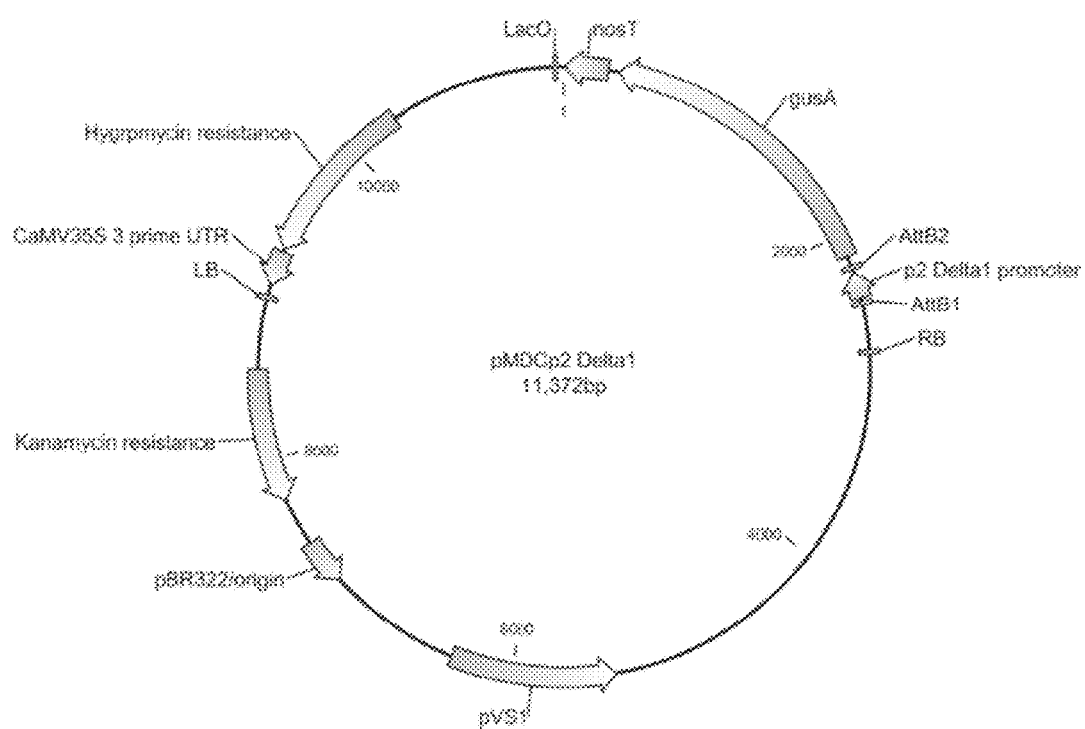
Figure 5B:
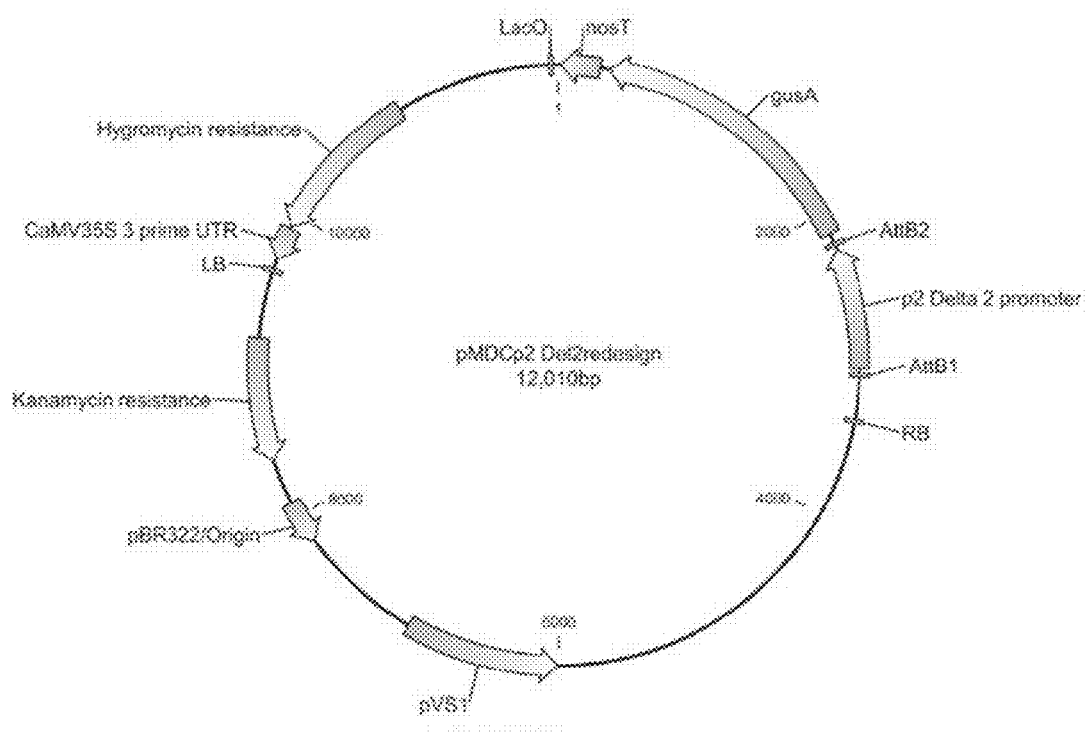

FIG. 5A-B depicts the vector map for pMDC p2Δ1, and p2Δ2 construct respectively, in accordance with an embodiment of the present disclosure.

Figure 6A:
Figure 6B:
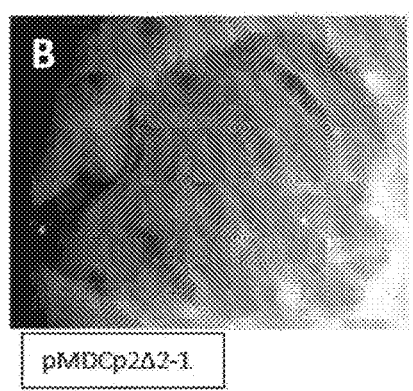

FIG. 6A-B depicts the histochemical GUS expression pattern in *Arabidopsis* plant driven by pMDCp2Δ1, and pMDCp2Δ2, in accordance with an embodiment of the present disclosure.

Figure 7:
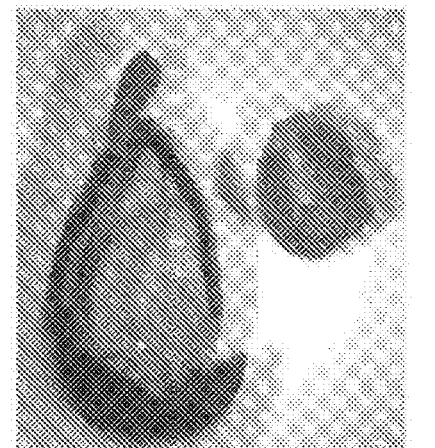

FIG. 7 depicts the histochemical GUS expression pattern in cotton p2 event (CT/pMDCp2-Exp.2-1B-1, in accordance with an embodiment of the present disclosure.

Figure 8:
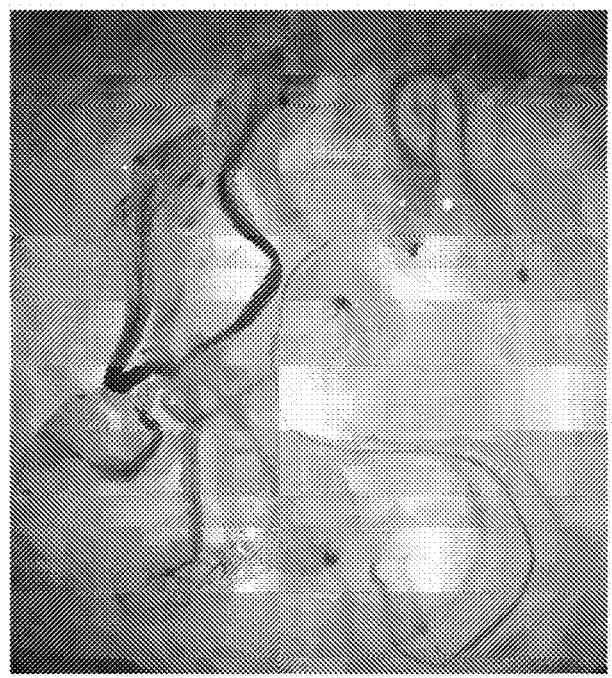

FIG. 8 depicts the histochemical GUS expression pattern in *Arabidopsis* p2 event T3 plant pMDCp2-1-4-1-4, in accordance with an embodiment of the present disclosure.

Figure 9:
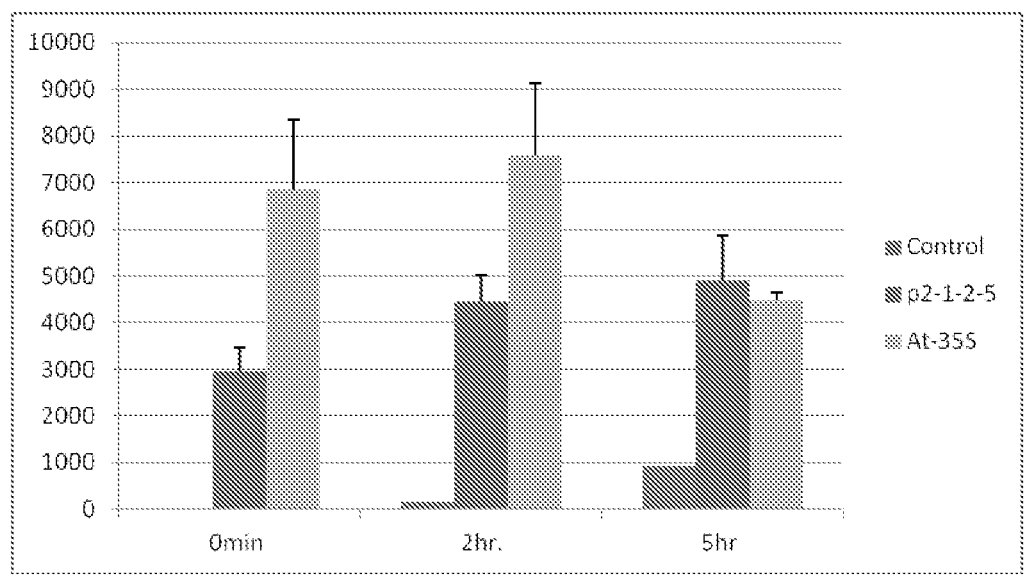

FIG. 9 depicts the effect of p2 promoter activity in *Arabidopsis* upon salt stress at various time points, in accordance with an embodiment of the present disclosure.

Figure 10:
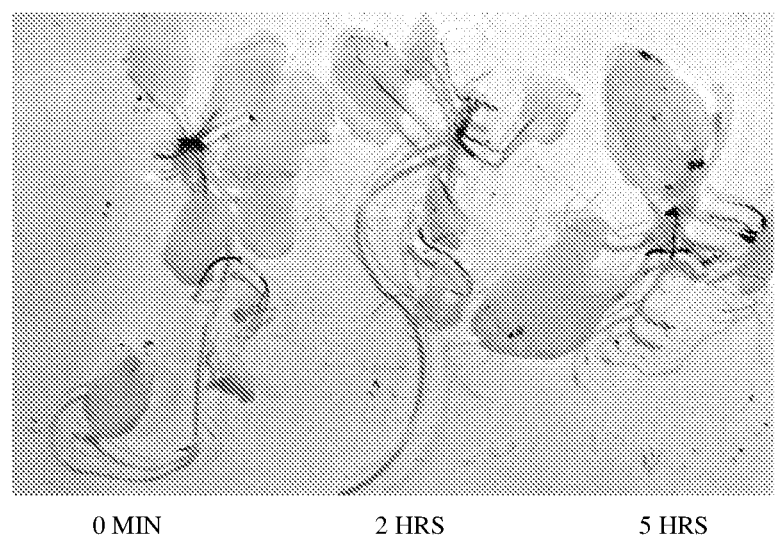

FIG. 10 depicts the histochemical GUS expression pattern driven by p2 in *Arabidopsis* whole plants upon salt stress at various time points, in accordance with an embodiment of the present disclosure.

Figure 11:
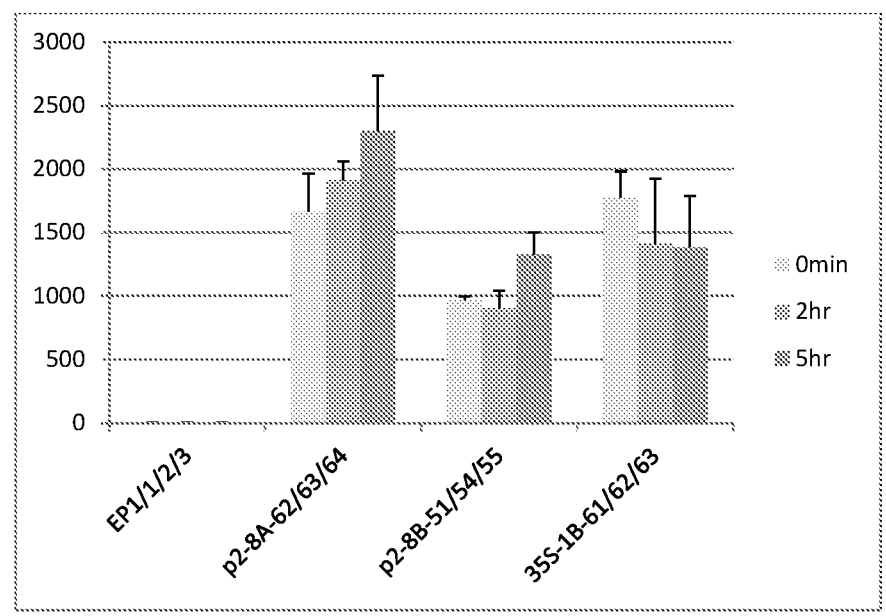

FIG. 11 depicts the effect of p2 promoter activity in rice upon salt stress at various time points, in accordance with an embodiment of the present disclosure.

Figure 12:
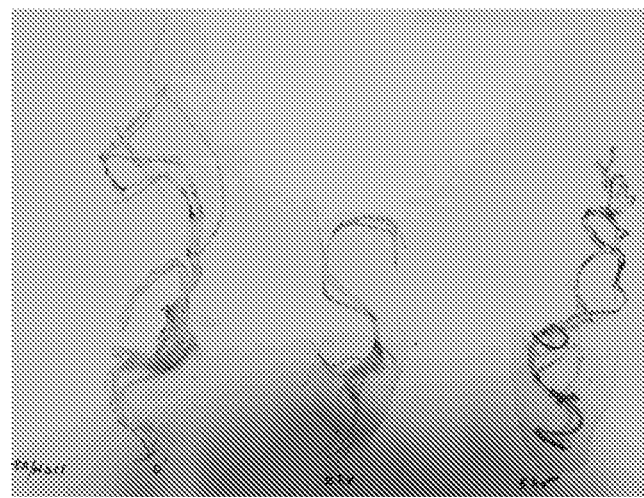

FIG. 12 depicts the histochemical GUS expression pattern driven by p2 in rice upon salt stress at various time points, in accordance with an embodiment of the present disclosure.

Figure 13:
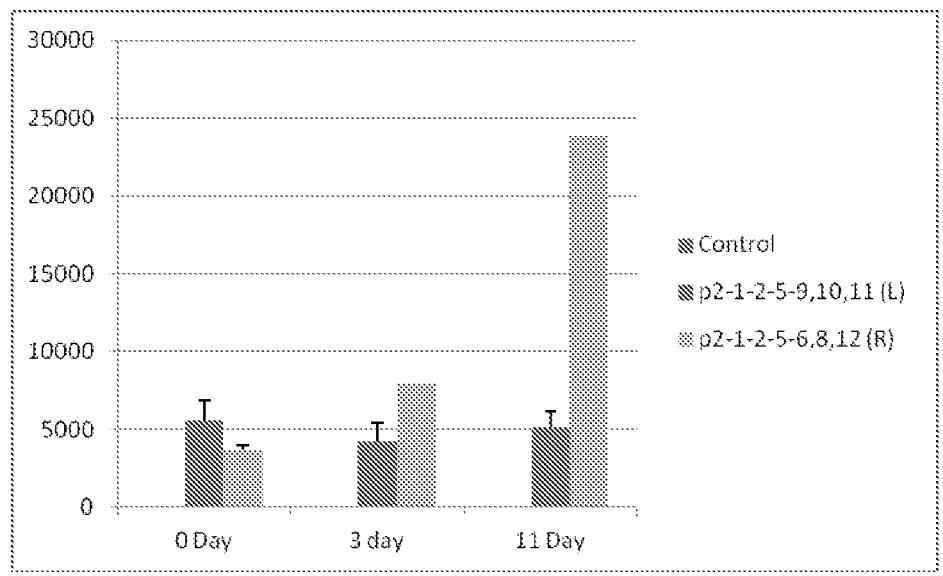

FIG. 13 depicts the effect of p2 promoter activity in *Arabidopsis* upon water stress at various time points, in accordance with an embodiment of the present disclosure.

Figure 14:
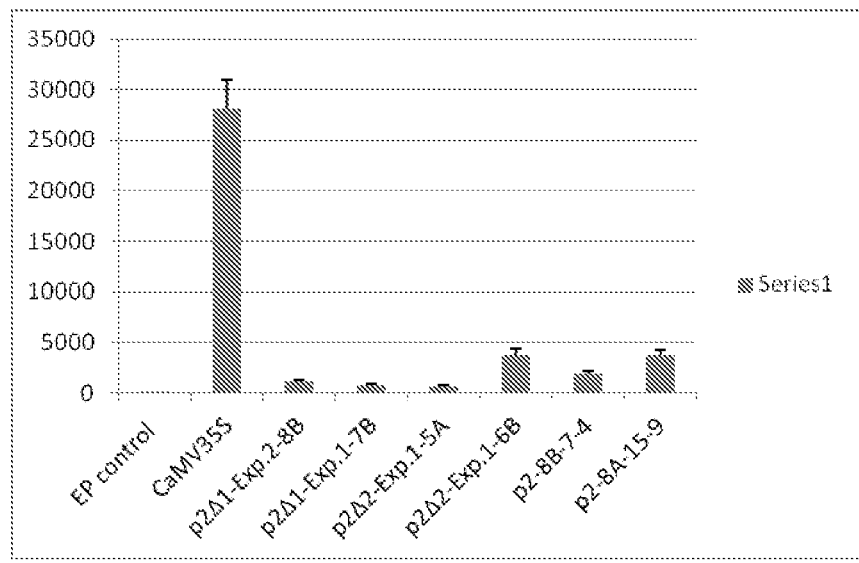

FIG. 14 depicts the GUS quantification from p2Δ1 and p2Δ2 rice transformants samples (leaf), in accordance with an embodiment of the present disclosure.

Figure 15:
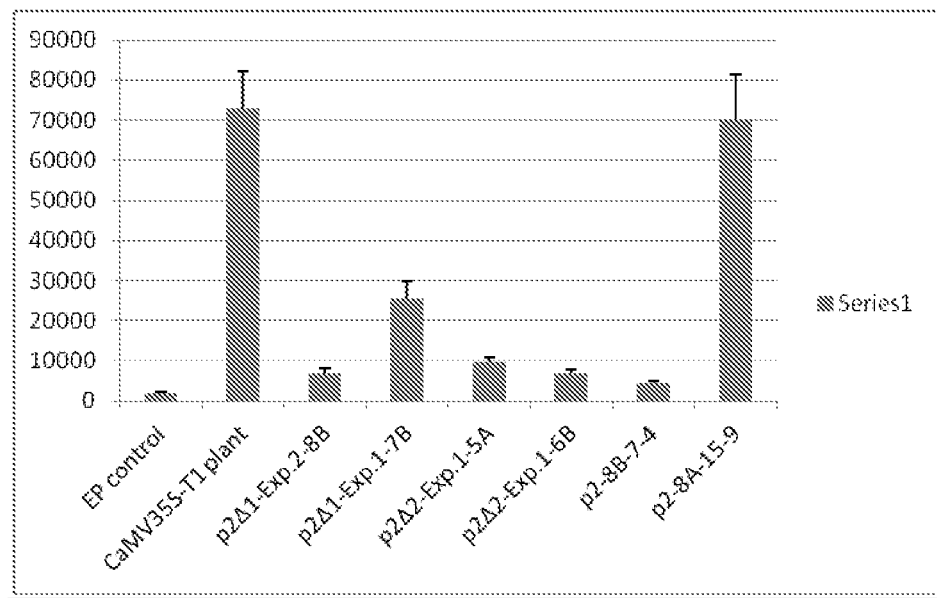

FIG. 15 depicts the GUS quantification from p2Δ1 and p2Δ2 rice transformants samples (root), in accordance with an embodiment of the present disclosure.

Figure 16:
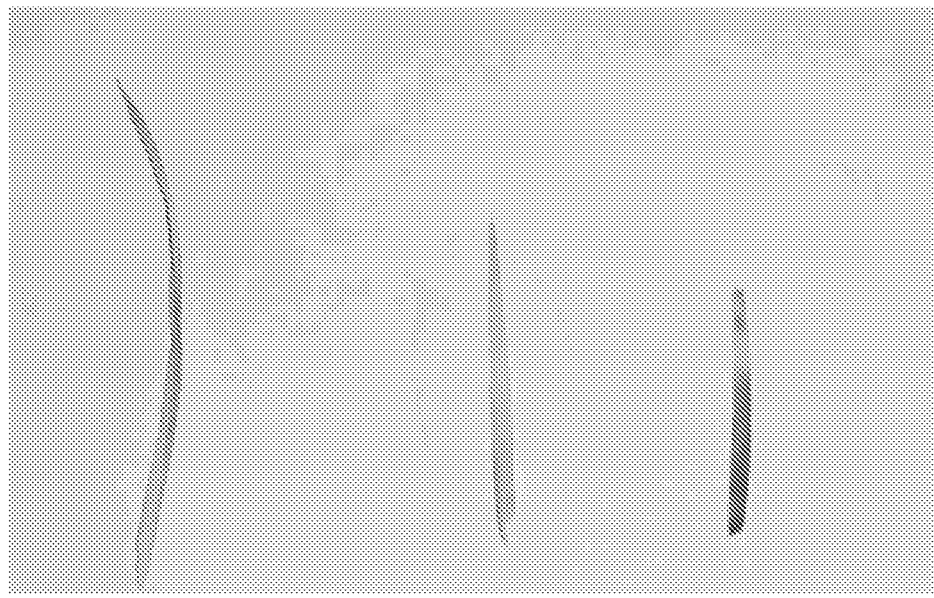

FIG. 16 depicts the histochemical GUS expression pattern in rice plant driven by pMDCp2, pMDCp2Δ1, and pMDCp2Δ2, in accordance with an embodiment of the present disclosure.

DETAILED DESCRIPTION OF THE INVENTION

Those skilled in the art will be aware that the disclosure described herein is subject to variations and modifications other than those specifically described. It is to be understood that the disclosure described herein includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, example and appended claims are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The term "plurality" means more than one.

The terms "at least two", "more than one" and "plurality" are used interchangeably.

The terms "comprise" and "comprising" are used in the inclusive, open sense, meaning that additional elements may be included. It is not intended to be construed as "consists of only.

Throughout this specification, unless the context requires otherwise the word "comprise", and variations such as "comprises" and "comprising", will be understood to imply the inclusion of a stated element or step or group of element or steps but not the exclusion of any other element or step or group of element or steps. The term "including" is used to mean "including but not limited to". "Including" and "including but not limited to" are used interchangeably.

The term "nucleotide sequence" means the order in which nucleotides are situated in a chain relative to one another.

The term "heterologous gene/DNA" refers to DNA sequence of foreign origin inserted into the plant genome.

The term "polynucleotide" or "polynucleotide molecule" or "polynucleotide sequence" used herein refers to the single or double stranded DNA or RNA of genomic or synthetic origin, i.e., a polymer of deoxyribonucleotide or ribonucleotide bases, respectively, read from the 5' (upstream) end to the 3' (downstream) end.

The term "nucleotide sequence" as used herein refers to the sequence of a polynucleotide molecule.

The term "promoter" as used herein, refers to a polynucleotide molecule that is in its native or non native state located upstream or 5' to a translational start codon of an open reading frame (or protein-coding region) and that is involved in recognition and binding of RNA polymerase II and other proteins (trans-acting transcription factors) to initiate transcription.

A "plant promoter" is a native or non-native promoter that is functional in plant cells. Constitutive plant promoters are functional in most or all tissues of a plant throughout plant development. Any plant promoter can be used as a 5' regulatory element for modulating expression of a particular gene or genes operably associated thereto. When operably linked to a polynucleotide molecule, a promoter typically causes the polynucleotide molecule to be transcribed in a manner that is similar to that of which the promoter is normally associated.

The terms "encoding" and "coding" refer to the process by which a polynucleotide, through the mechanisms of transcription and translation, provides information to a cell from which a series of amino acids can be assembled into a specific polypeptide. Because of the degeneracy of the genetic code, certain base changes in DNA sequence do not change the amino acid sequence of a protein.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence.

The phrase "altered expression" in reference to a polynucleotide indicates that the pattern of expression in, e.g., a transgenic plant or plant tissue, is different from the expression pattern in a wild-type plant of the same species. Thus, the polynucleotide of interest is expressed in a cell or tissue type other than a cell or tissue type in which the sequence is expressed in the wild type plant, or by expression at a time other than at the time the sequence is expressed in the wild type plant, or by a response to different inducible agents, such as hormones or environmental signals, or at different expression levels, compared with those found in a wild type plant. The resulting expression pattern can be transient or stable, constitutive or inducible. With reference to a polypeptide, "altered expression" further may relate to altered activity levels resulting either from altered protein levels or from interactions of the polypeptides with exogenous or endogenous modulators, or from interactions with factors or as a result of the chemical modification of the polypeptides.

The terms "exogenous nucleic acid" and "heterologous nucleic acid" are used interchangeably and refer to a nucleic acid, DNA or RNA, which has been introduced into a cell (or the cell's ancestor) through the efforts of humans. Such exogenous nucleic acid may be a copy of a sequence which is naturally found in the cell into which it was introduced, or fragments thereof.

The term "endogenous nucleic acid" refers to a nucleic acid, gene, polynucleotide, DNA, RNA, mRNA, or cDNA molecule that is present in a plant or organism that is to be genetically engineered. An endogenous sequence is "native" to, i.e., indigenous to, the plant or organism that is to be genetically engineered.

The phrase "homologous sequences" refers to polynucleotide or polypeptide sequences that are similar due to common ancestry and sequence conservation. Homologous sequences may be "orthologous," if they were separated by a speciation event, or "paralogous," if they were separated by a gene duplication event. The phrase "functional homolog" refers to a polynucleotide or polypeptide sequences that are similar due to common ancestry and sequence conservation and have identical or similar function at the catalytic, cellular, or organismal levels.

The term "recombinant DNA construct" means a molecule that is constructed outside living cells by joining natural or synthetic DNA to a DNA molecule that can replicate in a living cell.

A "vector" is any means by which a nucleic acid can be propagated and/or transferred between organisms, cells or cellular components. Vectors include viruses, bacteriophage, pro-viruses, plasmids, phagemids, transposons and artificial chromosomes such as YACs (yeast artificial chromosomes), BACs (bacterial artificial chromosomes), and PLACs (plant artificial chromosomes), and the like, that are "episomes", that is, that replicate autonomously or can integrate into a chromosome of a host cell. A vector can also be a naked RNA polynucleotide, a polynucleotide composed of both DNA and RNA within the same strand, a poly-lysine-conjugated DNA or RNA, a peptide conjugated DNA or RNA, a liposome-conjugated DNA, or the like, that are not episomal in nature, or it can be an organism which comprises one or more of the above polynucleotide constructs such as *Agrobacterium* or a bacterium.

The term "recombinant vector" means a vector carrying a foreign DNA fragment.

"Transformation" refers to the process by which a recombinant DNA molecule is introduced into a host cell. Transformation (or transduction, or transfection), can be achieved by any one of a number of means including electroporation, microinjection, biolistics (or particle bombardment-mediated delivery), or *Agrobacterium*-mediated transformation.

The term "recombinant host cell" means a host cell carrying a recombinant vector.

The term "transgenic plant" means plants that have been genetically engineered to artificially introduce a gene or set of gene sequences in the plant genome.

The term "p2" is designated to a nucleotide fragment having sequence as set forth in SEQ ID NO: 1 that shows promoter like activity.

The term "p2Δ1" is designated to a nucleotide fragment having sequence as set forth in SEQ ID NO: 9 that shows promoter like activity.

The term "p2Δ2" is designated to a nucleotide fragment having sequence as set forth in SEQ ID NO: 10 that shows promoter like activity.

Description of Sequences:

SEQ ID NO: 1 depicts 1956 bp long nucleotide sequence of constitutive plant promoter ("p2") from cotton.

```
TGACCAACTTTCCCCTAAGGTACGAGACTTTCTAAAGTCTCTCATTTC

CAGACCCTCTAAAGCCAATTTTGACCTATTGCTTTGACTCTTCATTTT

TCTTGAAATACTAATGTCTGATACACTCATGTCTAATATAGGTATAGG

GATATAACCTTCCCAGAATCCTCCAAATATATAGGAAAATATAGAAAA

AAATTTGAACATCCCCTTGTCAGATACTATGCTCCTTGGACCTGGGTG

TAGTGTAGTGTAAGGTATGGGTATAGTTAGATATTTCTTTTAAGTTTT

TTCATGTATTTGGAGAATCTTTTGATGTCAGATATCCATATCCATGTC

TCAGACACAAGTGGTGAACATGGTATTTCAACAAAAATGAAGTGTCGC

AACAACATTGGTCGGATATATATTGGTATCTGACACTCATGGATGAGT

TAGAGTTGACATGTTTTAAAGATTATGGGTTTCACATTACAGACGGAG

CTTTGCTCTCTTTTCTTGGTTGATGCTAAATTGGTATTGTGGTTATTG

CGCTAAAGTTAAGATGGTCGGTTTGAATGATGTACAGGCATGTGATAT
```

-continued

TAAAGACCCAAAGCAAAACATAGAGTGGACAGTGCCAGAAGGAGGAGG

TGGCCCAGGCTATTCAGTCATGTAGAATATATAAGCTAATCCCCTTTC

TTATCATTGCTCGTTGCAAATATAGTTCTACTTTTGTACTTTACAACA

AATACATTATCTTTGAAATAATTGGTAAGTCCCATCTTAATTGCTACA

AAAATTTAACTTTTTACTATACCAAATGAAAAGAAAGCTTTAAGGAGT

TCATGAAAGTTCATAATCTTGAGTCTTACCCCTGGATTTGCCTTCAAT

CTCAAGTAATCAAGGTTTTCCATTTAAATAACTGATTGTTAACGAGTC

AATATGACATAGAAGTCTAGCTAGTTTCTCAAGGCAATCCAGAATGGT

AAGCAGCTGTTAGAAATGTTTCGAATCAAGCGGTGGCCTCCAACAGGA

CTAAGGTTAAAGGTTTATACCAGAAAACCTCAAAATCCAACATCCTCC

CTCTTATCTGCGGATTGTGGATAAAGATGGGTCACCTGCTCTACGCTA

TTTTATTGATGAATATACTTTGTTTTCTTCTGCTTTTATGTTAATCAT

AGTTGTTTACTTTGTTAGTGAATAAACTGGTTATCATGCAGAGGAACA

AAAAAGAAAGGATAATTATATAGCTGAAACCTAATGACGTGTAGTCT

GTTAATAGACCACTAATAATTAATATTTTCAATCTTTGATAACATCAA

ATAAAAATACCATTTATTCCTTATCTATAAAAAGGACACATTATCAT

TATCACTTACATGTGAAATTATAATAAACTTTTTTACGTAATATTTTA

GCAAATCTTACAGCATTTTTGATTGGATTTATTTAAGTATGGTATATA

TTAATAAATATTTAACCGATAATTATAAAATTTTAAATATTAATTTAC

TTTAAATTTGACATGTATTATCTATATTAATGTACCATAAAATAGGAT

GCTAAAATATTAATAGTATAAATTATAAAGCGTATTTTACATCAATAT

AACTAGATATTTACTTAAATAATTATTTGATTAAAATTTAACAACGTA

TCCATTATATATGGTCATAATTGTAGAAAGAATAAATAACCATTGCAA

TTGAATATTGCAAAAGATGATTGAAATGTATGTGGTGTCATAGTGAT

GAGATACGTTGATAATGGGATTGGATTAGGACATCCAAAAGAAAGCT

TCTTTGATTTGCCACAAGTTCACATCCCGTGAGACTACAGTTTGGTTG

AACAATAATCTCAACACCCGACAGGACCCAAAGCAAATTCAGGGTTCA

CGGACTACTCTCCACCAAACTTTTCTCCATTCATTCCTCTATAAATAA

CAATCTCTGGGTAGCTTGCCACATCATAAAAAAAGT

SEQ ID NO: 2 depicts forward primer with PstI site and CACC site for generating SEQ ID NO: 1.

CACCTGCAGTGACCAACTTTCCCCTAAGGTACGAGACTT

SEQ ID NO: 3 depicts reverse primer with SacI site for generating SEQ ID NO: 1.

GAGCTCACTTTTTTTATGATGTGGCAAGCTACCCAG

SEQ ID NO: 5 depicts nucleotide sequence of CARGN-CAT motif identified in p2 promoter.

CCATAAAATAGG (SEQ ID NO: 6)

nucleotide sequence of CARGCW8GAT motif identified in p2 promoter.

ATAAAATAG

SEQ ID NO: 7 depicts nucleotide sequence of CIACADIANLELHC motif identified in p2 promoter.

CAAGGCAATC

SEQ ID NO: 8 depicts nucleotide sequence of PRECONSCRHSP70A motif identified in p2 promoter.

CCGATAATTATAAAATTTTAAATA

SEQ ID NO: 9 depicts deletion fragment p2Δ1 of p2 promoter.

TCCCGTGAGACTACAGTTTGGTTGAACAATAATCTCAACACCCGACAG

GACCCAAAGCAAATTCAGGGTTCACGGACTACTCTCCACCAAACTTTT

CTCCATTCATTCCTCTATAAATAACAATCTCTGGGTAGCTTGCCACAT

CATAAAAAAAGT

SEQ ID NO: 10 depicts deletion fragment p2Δ2 of p2 promoter.

TGGTTATCATGCAGAGGAACAAAAAAGAAAAGGATAATTATATAGCTG

AAACCTAATGACGTGTAGTCTGTTAATAGACCACTAATAATTAATATT

TTCAATCTTTGATAACATCAAATAAAAATACCATTTATTCCTTATCTA

TAAAAAAGGACACATTATCATTATCACTTACATGTGAAATTATAATAA

ACTTTTTTACGTAATATTTTAGCAAATCTTACAGCATTTTTGATTGGA

TTTATTTAAGTATGGTATATATTAATAAATATTTAACCGATAATTATA

AAATTTTAAATATTAATTTACTTTAAATTTGACATGTATTATCTATAT

TAATGTACCATAAAATAGGATGCTAAAATATTAATAGTATAAATTATA

AAGCGTATTTTACATCAATATAACTAGATATTTACTTAAATAATTATT

TGATTAAAATTTAACAACGTATCCATTATATATGGTCATAATTGTAGA

AAGAATAAATAACCATTGCAATTGAATATTGCAAAAGATGATTGAAAA

TGTATGTGGTGTCATAGTGATGAGATACGTTGATAATGGGATTGGATT

AGGACATCCAAAAGAAAGCTTCTTTGATTTGCCACAAGTTCACATCC

CGTGAGACTACAGTTTGGTTGAACAATAATCTCAACACCCGACAGGAC

CCAAAGCAAATTCAGGGTTCACGGACTACTCTCCACCAAACTTTTCTC

CATTCATTCCTCTATAAATAACAATCTCTGGGTAGCTTGCCACATCAT

AAAAAAAGT

SEQ ID NO: 11 depicts forward primer sequence to amplify SEQ ID NO: 9.

TCCCGTGAGACTACAGTTTGG

SEQ ID NO: 12 depicts reverse primer sequence to amplify SEQ ID NO: 9 or SEQ ID NO: 10.

GGTAGCTTGCCACATCATAAAAAAAGT

SEQ ID NO: 13 depicts forward primer sequence to amplify SEQ ID NO: 10.

TGGTTATCATGCAGAGGAA

In an embodiment of the present disclosure, there is provided a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1.

In an embodiment of the present disclosure, there is provided a promoter capable of driving or regulating expression of an operably linked gene of interest in a constitutive or stress inducible manner, comprising a DNA fragment as set forth in SEQ ID NO: 1 or complement thereof.

In an embodiment of the present disclosure, there is provided a promoter capable of driving or regulating expression of an operably linked gene of interest in a stress inducible manner, comprising a DNA fragment as set forth in SEQ ID NO: 1 or complement thereof.

In an embodiment of the present disclosure, there is provided a promoter capable of driving or regulating expression of an operably linked gene of interest in a constitutive manner, comprising a DNA fragment as set forth in SEQ ID NO: 1 or complement thereof.

In an embodiment of the present disclosure, there is provided a promoter capable of driving or regulating expression of an operably linked gene of interest in a constitutive or stress inducible manner, comprising a DNA fragment having at least 90% sequence identity to any contiguous stretch of DNA sequence as set forth in SEQ ID NO: 1.

In an embodiment of the present disclosure, there is provided a promoter capable of driving or regulating expression of an operably linked gene of interest in a constitutive manner, comprising a DNA fragment having at least 90% sequence identity to any contiguous stretch of DNA sequence as set forth in SEQ ID NO: 1.

In an embodiment of the present disclosure, there is provided a promoter capable of driving or regulating expression of an operably linked gene of interest in a stress inducible manner, comprising a DNA fragment having at least 90% sequence identity to any contiguous stretch of DNA sequence as set forth in SEQ ID NO: 1.

In an embodiment of the present disclosure, there is provided a promoter capable of driving or regulating expression of an operably linked gene of interest in a constitutive or stress inducible manner, comprising a DNA fragment capable of hybridizing under stringent conditions with any contiguous stretch of DNA sequence as set in SEQ ID NO: 1.

In an embodiment of the present disclosure, there is provided a promoter capable of driving or regulating expression of an operably linked gene of interest in a constitutive manner, comprising a DNA fragment capable of hybridizing under stringent conditions with any contiguous stretch of DNA sequence as set in SEQ ID NO: 1.

In an embodiment of the present disclosure, there is provided a promoter capable of driving or regulating expression of an operably linked gene of interest in a stress inducible manner, comprising a DNA fragment capable of hybridizing under stringent conditions with any contiguous stretch of DNA sequence as set in SEQ ID NO: 1.

In an embodiment of the present disclosure, there is provided a promoter as described herein, wherein said stress is water stress.

In an embodiment of the present disclosure, there is provided a promoter as described herein, wherein said stress is salt stress.

In an embodiment of the present disclosure, there is provided a promoter as described herein, wherein said promoter sequence is as set forth in SEQ ID NO: 1.

In an embodiment of the present disclosure, there is provided a promoter as described herein, wherein said promoter sequence is as set forth in SEQ ID NO: 9.

In an embodiment of the present disclosure, there is provided a promoter as described herein, wherein said promoter sequence is as set forth in SEQ ID NO: 10.

In an embodiment of the present disclosure, there is provided a DNA construct comprising a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a DNA construct comprising a promoter capable of driving or regulating expression of an operably linked gene of interest in a constitutive manner, said promoter operably linked to a heterologous nucleic acid sequence.

In an embodiment of the present disclosure, there is provided a DNA construct comprising a promoter capable of driving or regulating expression of an operably linked gene of interest in a stress inducible manner, said promoter comprising a DNA fragment as set forth in SEQ ID NO: 1 or complement thereof, wherein said DNA fragment is operably linked to a heterologous nucleic acid sequence.

In an embodiment of the present disclosure, there is provided a DNA construct comprising a promoter capable of driving or regulating expression of an operably linked gene of interest in a constitutive manner, said promoter comprising a DNA fragment having at least 90% sequence identity to any contiguous stretch of DNA sequence as set forth in SEQ ID NO: 1, wherein said DNA fragment is operably linked to a heterologous nucleic acid sequence.

In an embodiment of the present disclosure, there is provided a DNA construct comprising a promoter capable of driving or regulating expression of an operably linked gene of interest in a stress inducible manner, said promoter comprising a DNA fragment having at least 90% sequence identity to any contiguous stretch of DNA sequence as set forth in SEQ ID NO: 1, wherein said DNA fragment is operably linked to a heterologous nucleic acid sequence.

In an embodiment of the present disclosure, there is provided a DNA construct comprising a promoter capable of driving or regulating expression of an operably linked gene of interest in a constitutive manner, said promoter comprising a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a DNA construct comprising a promoter capable of driving or regulating expression of an operably linked gene of interest in a stress inducible manner, said promoter comprising a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a DNA construct as described herein, wherein said stress is salt stress.

In an embodiment of the present disclosure, there is provided a DNA construct as described herein, wherein said stress is water stress.

In an embodiment of the present disclosure, there is provided a DNA construct as described herein, wherein said promoter sequence is as set forth in SEQ ID NO: 1.

In an embodiment of the present disclosure, there is provided a DNA construct as described herein, wherein said promoter sequence is as set forth in SEQ ID NO: 9.

In an embodiment of the present disclosure, there is provided a DNA construct as described herein, wherein said promoter sequence is as set forth in SEQ ID NO: 10.

In an embodiment of the present disclosure, there is provided a DNA vector comprising a DNA construct, said DNA construct comprising a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a DNA vector comprising a DNA construct, said DNA construct comprising a promoter capable of driving or regulating expression of an operably linked gene of interest in a constitutive manner, comprising: (a) a DNA fragment as set forth in SEQ ID NO: 1 or complement thereof, wherein said DNA fragment is operably linked to a heterologous nucleic acid sequence.

In an embodiment of the present disclosure, there is provided a DNA vector comprising a DNA construct, said DNA construct comprising a promoter capable of driving or regulating expression of an operably linked gene of interest in a stress inducible manner, comprising: (a) a DNA fragment as set forth in SEQ ID NO: 1 or complement thereof, wherein said DNA fragment is operably linked to a heterologous nucleic acid sequence.

In an embodiment of the present disclosure, there is provided a DNA vector comprising a DNA construct, said DNA construct comprising a promoter capable of driving or regulating expression of an operably linked gene of interest in a constitutive manner, comprising a DNA fragment having at least 90% sequence identity to any contiguous stretch of DNA sequence as set forth in SEQ ID NO: 1, wherein said DNA fragment is operably linked to a heterologous nucleic acid sequence.

In an embodiment of the present disclosure, there is provided a DNA vector comprising a DNA construct, said DNA construct comprising a promoter capable of driving or regulating expression of an operably linked gene of interest in stress inducible manner, comprising a DNA fragment having at least 90% sequence identity to any contiguous stretch of DNA sequence as set forth in SEQ ID NO: 1, wherein said DNA fragment is operably linked to a heterologous nucleic acid sequence.

In an embodiment of the present disclosure, there is provided a DNA vector comprising a DNA construct, said DNA construct comprising a promoter capable of driving or regulating expression of an operably linked gene of interest in a constitutive manner, comprising a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a DNA vector comprising a DNA construct, said DNA construct comprising a promoter capable of driving or regulating expression of an operably linked gene of interest in a stress inducible manner, comprising a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a DNA vector as described herein, wherein said stress is salt stress.

In an embodiment of the present disclosure, there is provided a DNA vector as described herein, wherein said stress is water stress.

In an embodiment of the present disclosure, there is provided a DNA vector as described herein, wherein said promoter sequence is as set forth in SEQ ID NO: 1.

In an embodiment of the present disclosure, there is provided a DNA vector as described herein, wherein said promoter sequence is as set forth in SEQ ID NO: 9.

In an embodiment of the present disclosure, there is provided a DNA vector as described herein, wherein said promoter sequence is as set forth in SEQ ID NO: 10.

In an embodiment of the present disclosure, there is provided a recombinant host cell comprising a DNA construct, said DNA construct comprising a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a recombinant host cell comprising a DNA construct, said DNA construct comprising a promoter capable of driving or regulating expression of an operably linked gene of interest in a constitutive manner, comprising a DNA fragment as set forth in SEQ ID NO: 1 or complement thereof, wherein said DNA fragment is operably linked to a heterologous nucleic acid sequence.

In an embodiment of the present disclosure, there is provided a recombinant host cell comprising a DNA construct, said DNA construct comprising a promoter capable of driving or regulating expression of an operably linked gene of interest in a stress inducible manner, comprising a DNA fragment as set forth in SEQ ID NO: 1 or complement thereof, wherein said DNA fragment is operably linked to a heterologous nucleic acid sequence.

In an embodiment of the present disclosure, there is provided a recombinant host cell comprising a DNA construct, said DNA construct comprising a promoter capable of driving or regulating expression of an operably linked gene of interest in a constitutive manner, comprising: a DNA fragment having at least 90% sequence identity to any contiguous stretch of DNA sequence as set forth in SEQ ID NO: 1, wherein said DNA fragment is operably linked to a heterologous nucleic acid sequence.

In an embodiment of the present disclosure, there is provided a recombinant host cell comprising a DNA construct, said DNA construct comprising a promoter capable of driving or regulating expression of an operably linked gene of interest in a stress inducible manner, comprising: a DNA fragment having at least 90% sequence identity to any contiguous stretch of DNA sequence as set forth in SEQ ID NO: 1, wherein said DNA fragment is operably linked to a heterologous nucleic acid sequence.

In an embodiment of the present disclosure, there is provided a recombinant host cell comprising a DNA construct, said DNA construct comprising a promoter capable of driving or regulating expression of an operably linked gene of interest in a constitutive manner, comprising a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a recombinant host cell comprising a DNA construct, said DNA construct comprising a promoter capable of driving or regulating expression of an operably linked gene of interest in a stress inducible manner, comprising a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a recombinant host cell comprising a DNA construct as described herein, wherein said stress is salt stress.

In an embodiment of the present disclosure, there is provided a recombinant host cell comprising a DNA construct as described herein, wherein said stress is water stress.

In an embodiment of the present disclosure, there is provided a recombinant host cell comprising a DNA construct as described herein, wherein said promoter sequence is as set forth in SEQ ID NO: 1.

In an embodiment of the present disclosure, there is provided a recombinant host cell comprising a DNA construct as described herein, wherein said promoter sequence is as set forth in SEQ ID NO: 9.

In an embodiment of the present disclosure, there is provided a recombinant host cell comprising a DNA construct as described herein, wherein said promoter sequence is as set forth in SEQ ID NO: 10.

In an embodiment of the present disclosure, there is provided a recombinant host cell comprising a DNA construct as described herein, wherein said recombinant host cell is of bacterial origin.

In an embodiment of the present disclosure, there is provided a recombinant host cell comprising a DNA construct as described herein, wherein said recombinant host cell is *Agrobacterium tumefaciens*.

In an embodiment of the present disclosure, there is provided a recombinant host cell comprising a DNA construct as described herein, wherein said recombinant host cell is *E. coli*.

In an embodiment of the present disclosure, there is provided a recombinant host cell comprising a DNA construct as described herein, wherein said recombinant host cell is of fungal origin.

In an embodiment of the present disclosure, there is provided a recombinant host cell comprising a DNA construct as described herein, wherein said recombinant host cell is of plant origin.

In an embodiment of the present disclosure, there is provided a recombinant host cell comprising a DNA construct as described herein, wherein said recombinant host cell is a monocot.

In an embodiment of the present disclosure, there is provided a recombinant host cell comprising a DNA construct as described herein, wherein said recombinant host cell is a dicot.

In an embodiment of the present disclosure, there is provided a recombinant host cell comprising a DNA construct as described herein, wherein said recombinant host cell is rice.

In an embodiment of the present disclosure, there is provided a recombinant host cell comprising a DNA vector comprising a DNA construct, said DNA construct comprising a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a recombinant host cell comprising a DNA vector comprising a DNA construct, said DNA construct comprising a promoter capable of driving or regulating expression of an operably linked gene of interest in a constitutive manner, comprising: (a) a DNA fragment as set forth in SEQ ID NO: 1 or complement thereof, wherein said DNA fragment is operably linked to a heterologous nucleic acid sequence.

In an embodiment of the present disclosure, there is provided a recombinant host cell comprising a DNA vector comprising a DNA construct, said DNA construct comprising a promoter capable of driving or regulating expression of an operably linked gene of interest in a stress inducible manner, comprising: (a) a DNA fragment as set forth in SEQ ID NO: 1 or complement thereof, wherein said DNA fragment is operably linked to a heterologous nucleic acid sequence.

In an embodiment of the present disclosure, there is provided a recombinant host cell comprising a DNA vector comprising a DNA construct, said DNA construct comprising a promoter capable of driving or regulating expression of an operably linked gene of interest in a constitutive manner, comprising a DNA fragment having at least 90% sequence identity to any contiguous stretch of DNA sequence as set forth in SEQ ID NO: 1, wherein said DNA fragment is operably linked to a heterologous nucleic acid sequence.

In an embodiment of the present disclosure, there is provided a recombinant host cell comprising a DNA vector comprising a DNA construct, said DNA construct comprising a promoter capable of driving or regulating expression of an operably linked gene of interest in a stress inducible manner, comprising a DNA fragment having at least 90% sequence identity to any contiguous stretch of DNA sequence as set forth in SEQ ID NO: 1, wherein said DNA fragment is operably linked to a heterologous nucleic acid sequence.

In an embodiment of the present disclosure, there is provided a recombinant host cell comprising a DNA vector comprising a DNA construct, said DNA construct comprising a promoter capable of driving or regulating expression of an operably linked gene of interest in a constitutive manner, comprising a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a recombinant host cell comprising a DNA vector comprising a DNA construct, said DNA construct comprising a promoter capable of driving or regulating expression of an operably linked gene of interest in a stress inducible manner, comprising a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a recombinant host cell comprising a DNA vector as described herein, wherein said stress is salt stress.

In an embodiment of the present disclosure, there is provided a recombinant host cell comprising a DNA vector as described herein, wherein said stress is water stress.

In an embodiment of the present disclosure, there is provided a recombinant host cell comprising a DNA vector as described herein, wherein said promoter sequence is as set forth in SEQ ID NO: 1.

In an embodiment of the present disclosure, there is provided a recombinant host cell comprising a DNA vector as described herein, wherein said promoter sequence is as set forth in SEQ ID NO: 9.

In an embodiment of the present disclosure, there is provided a recombinant host cell comprising a DNA vector as described herein, wherein said promoter sequence is as set forth in SEQ ID NO: 10.

In an embodiment of the present disclosure, there is provided a recombinant host cell comprising a DNA vector as described herein, wherein said recombinant cell is of bacterial origin.

In an embodiment of the present disclosure, there is provided a recombinant host cell comprising a DNA vector as described herein, wherein said recombinant cell is *E. coli*.

In an embodiment of the present disclosure, there is provided a recombinant host cell comprising a DNA vector as described herein, wherein said recombinant cell is *Agrobacterium tumefaciens*.

In an embodiment of the present disclosure, there is provided a recombinant host cell comprising a DNA vector as described herein, wherein said recombinant cell is of fungal origin.

In an embodiment of the present disclosure, there is provided a transgenic plant or part thereof, including seeds, comprising within its genome, a DNA construct comprising a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a transgenic plant or part thereof, including seeds, comprising within its genome, a DNA construct comprising a promoter capable of driving or regulating expression of an operably linked gene of interest in a constitutive manner, comprising: (a) a DNA fragment as set forth in SEQ ID NO: 1 or complement thereof, wherein said DNA fragment is operably linked to a heterologous nucleic acid sequence.

In an embodiment of the present disclosure, there is provided a transgenic plant or part thereof, including seeds, comprising within its genome, a DNA construct comprising a promoter capable of driving or regulating expression of an operably linked gene of interest in a stress inducible manner, comprising: (a) a DNA fragment as set forth in SEQ ID NO: 1 or complement thereof, wherein said DNA fragment is operably linked to a heterologous nucleic acid sequence.

In an embodiment of the present disclosure, there is provided a transgenic plant or part thereof, including seeds, comprising within its genome, a DNA construct comprising a promoter capable of driving or regulating expression of an operably linked gene of interest in a constitutive manner, comprising a DNA fragment having at least 90% sequence identity to any contiguous stretch of DNA sequence as set forth in SEQ ID NO: 1, wherein said DNA fragment is operably linked to a heterologous nucleic acid sequence.

In an embodiment of the present disclosure, there is provided a transgenic plant or part thereof, including seeds, comprising within its genome, a DNA construct comprising a promoter capable of driving or regulating expression of an operably linked gene of interest in a stress inducible manner, comprising a DNA fragment having at least 90% sequence identity to any contiguous stretch of DNA sequence as set forth in SEQ ID NO: 1, wherein said DNA fragment is operably linked to a heterologous nucleic acid sequence.

In an embodiment of the present disclosure, there is provided a transgenic plant or part thereof, including seeds, comprising within its genome, a DNA construct comprising a promoter capable of driving or regulating expression of an operably linked gene of interest in a constitutive manner, comprising a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a transgenic plant or part thereof, including seeds, comprising within its genome, a DNA construct comprising a promoter capable of driving or regulating expression of an operably linked gene of interest in a stress inducible manner, comprising a DNA fragment capable of hybridizing under stringent conditions with any contiguous stretch of DNA sequence as set in SEQ ID NO: 1, wherein said DNA fragment is operably linked to a heterologous nucleic acid sequence.

In an embodiment of the present disclosure, there is provided a transgenic plant or parts thereof, including seeds, capable of expression of a gene of interest driven heterologously by a promoter capable of driving or regulating expression of an operably linked gene of interest in a constitutive or stress inducible manner, comprising: (a) a DNA fragment as set forth in SEQ ID NO: 1 or complement thereof; or (b) a DNA fragment having at least 90% sequence identity to any contiguous stretch of DNA sequence as set forth in SEQ ID NO: 1; or (c) a DNA fragment capable of hybridizing under stringent conditions with any contiguous stretch of DNA sequence as set in SEQ ID NO: 1.

In an embodiment of the present disclosure, there is provided a transgenic plant or parts thereof, including seeds, capable of expression of a gene of interest driven heterologously by a promoter capable of driving or regulating expression of an operably linked gene of interest in a constitutive manner, comprising a DNA fragment as set forth in SEQ ID NO: 1 or complement thereof.

In an embodiment of the present disclosure, there is provided a transgenic plant or parts thereof, including seeds, capable of expression of a gene of interest driven heterologously by a promoter capable of driving or regulating expression of an operably linked gene of interest in a stress inducible manner, comprising a DNA fragment as set forth in SEQ ID NO: 1 or complement thereof.

In an embodiment of the present disclosure, there is provided a transgenic plant or parts thereof, including seeds, capable of expression of a gene of interest driven heterologously by a promoter capable of driving or regulating expression of an operably linked gene of interest in a constitutive manner, comprising a DNA fragment having at least 90% sequence identity to any contiguous stretch of DNA sequence as set forth in SEQ ID NO: 1.

In an embodiment of the present disclosure, there is provided a transgenic plant or parts thereof, including seeds, capable of expression of a gene of interest driven heterologously by a promoter capable of driving or regulating expression of an operably linked gene of interest in a stress inducible manner, comprising a DNA fragment having at least 90% sequence identity to any contiguous stretch of DNA sequence as set forth in SEQ ID NO: 1.

In an embodiment of the present disclosure, there is provided a transgenic plant or parts thereof, including seeds, capable of expression of a gene of interest driven heterologously by a promoter capable of driving or regulating expression of an operably linked gene of interest in a constitutive manner, comprising a DNA fragment capable of hybridizing under stringent conditions with any contiguous stretch of DNA sequence as set in SEQ ID NO: 1.

In an embodiment of the present disclosure, there is provided a transgenic plant or parts thereof, including seeds, capable of expression of a gene of interest driven heterologously by a promoter capable of driving or regulating expression of an operably linked gene of interest in a stress inducible manner, comprising a DNA fragment capable of hybridizing under stringent conditions with any contiguous stretch of DNA sequence as set in SEQ ID NO: 1.

In an embodiment of the present disclosure, there is provided a transgenic plant or parts thereof, including seeds as described herein, wherein said stress is water stress.

In an embodiment of the present disclosure, there is provided a transgenic plant or parts thereof, including seeds as described herein, wherein said stress is salt stress.

In an embodiment of the present disclosure, there is provided a transgenic plant or parts thereof, including seeds as described herein, wherein said promoter sequence is as set forth in SEQ ID NO: 1.

In an embodiment of the present disclosure, there is provided a transgenic plant or parts thereof, including seeds as described herein, wherein said promoter sequence is as set forth in SEQ ID NO: 9.

In an embodiment of the present disclosure, there is provided a transgenic plant or parts thereof, including seeds as described herein, wherein said promoter sequence is as set forth in SEQ ID NO: 10.

In an embodiment of the present disclosure, there is provided a transgenic plant or parts thereof, including seeds as described herein, wherein said transgenic plants or parts thereof, including seeds is a monocot.

In an embodiment of the present disclosure, there is provided a transgenic plant or parts thereof, including seeds as described herein, wherein said transgenic plants or parts thereof, including seeds is a dicot.

In an embodiment of the present disclosure, there is provided a transgenic plant or parts thereof, including seeds as described herein, wherein said transgenic plants or parts thereof, including seeds is rice.

In an embodiment of the present disclosure, there is provided a transgenic plant or parts thereof, including seeds as described herein, wherein said transgenic plants or parts thereof, including seeds is *Arabidopsis thaliana*.

In an embodiment of the present disclosure, there is provided a method of generating a transgenic plant as described herein, said method comprising the steps: (a) obtaining plant cell(s); (b) obtaining a DNA construct as described herein; or a recombinant host cell comprising a DNA vector as described herein; (c) transforming said plant cell(s) with said DNA construct; or said recombinant host cell; and (d) selecting transformed plant cell(s) expressing said gene of interest.

In an embodiment of the present disclosure, there is provided a method of generating a transgenic plant as described herein, said method comprising the steps: (a) obtaining plant cell(s); (b) obtaining a DNA construct as described herein; (c) transforming said plant cell(s) with said DNA construct and (d) selecting transformed plant cell(s) expressing said gene of interest.

In an embodiment of the present disclosure, there is provided a method of generating a transgenic plant as described herein, said method comprising the steps: (a) obtaining plant cell(s); (b) obtaining a recombinant host cell comprising a DNA vector as described herein; (c) transforming said plant cell(s) with said recombinant host cell; and (d) selecting transformed plant cell(s) expressing said gene of interest.

In an embodiment of the present disclosure, there is provided a method of generating a transgenic plant as described herein, wherein said plant cell(s) is monocot.

In an embodiment of the present disclosure, there is provided a method of generating a transgenic plant as described herein, wherein said plant cell(s) is dicot.

In an embodiment of the present disclosure, there is provided a method of generating a transgenic plant as described herein, wherein said plant cell(s) is rice.

In an embodiment of the present disclosure, there is provided a method of generating a transgenic plant as described herein, wherein said promoter sequence is as set forth in SEQ ID NO: 1.

In an embodiment of the present disclosure, there is provided a method of generating a transgenic plant as described herein, wherein said promoter sequence is as set forth in SEQ ID NO: 9.

In an embodiment of the present disclosure, there is provided a method of generating a transgenic plant as described herein, wherein said promoter sequence is as set forth in SEQ ID NO: 10.

In an embodiment of the present disclosure, there is provided a method of generating a transgenic plant as described herein, wherein said gene of interest expression is root specific.

In an embodiment of the present disclosure, there is provided a method of generating a transgenic plant as described herein, wherein said gene of interest expression is constitutive.

In an embodiment of the present disclosure, there is provided a method of generating a transgenic plant as described herein, wherein said gene of interest expression is regulated in response to salt or water stress.

In an embodiment of the present disclosure, there is provided a method of generating a transgenic plant as described herein, wherein said gene of interest expression is regulated in response to salt stress.

In an embodiment of the present disclosure, there is provided a method of generating a transgenic plant as described herein, wherein said gene of interest expression is regulated in response to water stress.

In an embodiment of the present disclosure, there is provided a method of generating a transgenic plant as described herein, wherein said gene of interest expression is regulated in response to salt and water stress.

In an embodiment of the present disclosure, there is provided a method of generating a transgenic plant as described herein, wherein said transformation is carried out by a method selected from the group consisting of *Agrobacterium* mediated transformation method, particle gun bombardment method, in-planta transformation method, liposome mediated transformation method, protoplast transformation method, microinjection method, and macroinjection method.

In an embodiment of the present disclosure, there is provided a method of generating a transgenic plant as described herein, wherein said transformation is *Agrobacterium* mediated transformation method.

In an embodiment of the present disclosure, there is provided a method of heterologous expression of a gene of interest driven by a promoter as described herein, said method comprising the steps: (a) obtaining a DNA construct as described herein; or a recombinant host cell as described herein; (b) transforming plant cell(s) with said DNA construct, or said recombinant host cell to obtain transformed plant cell(s); and (c) selecting transformed plant cell(s) heterologously expressing said gene of interest.

In an embodiment of the present disclosure, there is provided a method of heterologous expression of a gene of interest driven by a promoter as described herein, said method comprising the steps: (a) obtaining a DNA construct as described herein; (b) transforming plant cell(s) with said DNA construct; and (c) selecting transformed plant cell(s) heterologously expressing said gene of interest.

In an embodiment of the present disclosure, there is provided a method of heterologous expression of a gene of interest driven by a promoter as described herein, said method comprising the steps: (a) a recombinant host cell as described herein; (b) transforming plant cell(s) with said recombinant host cell to obtain transformed plant cell(s); and (c) selecting transformed plant cell(s) heterologously expressing said gene of interest.

In an embodiment of the present disclosure, there is provided a method of heterologous expression of a gene of interest driven by a promoter as described herein, wherein said plant cell(s) is monocot.

In an embodiment of the present disclosure, there is provided a method of heterologous expression of a gene of interest driven by a promoter as described herein, wherein said plant cell(s) is dicot.

In an embodiment of the present disclosure, there is provided a method of heterologous expression of a gene of interest driven by a promoter as described herein, wherein said plant cell(s) is rice.

In an embodiment of the present disclosure, there is provided a method of heterologous expression of a gene of interest driven by a promoter as described herein, wherein said promoter sequence is as set forth in SEQ ID NO: 1.

In an embodiment of the present disclosure, there is provided a method of heterologous expression of a gene of interest driven by a promoter as described herein, wherein said promoter sequence is as set forth in SEQ ID NO: 9.

In an embodiment of the present disclosure, there is provided a method of heterologous expression of a gene of interest driven by a promoter as described herein, wherein said promoter sequence is as set forth in SEQ ID NO: 10.

In an embodiment of the present disclosure, there is provided a method of heterologous expression of a gene of interest driven by a promoter as described herein, wherein said gene of interest expression is constitutive.

In an embodiment of the present disclosure, there is provided a method of heterologous expression of a gene of interest driven by a promoter as described herein, wherein said gene of interest expression is regulated by water stress.

In an embodiment of the present disclosure, there is provided a method of heterologous expression of a gene of interest driven by a promoter as described herein, wherein said gene of interest expression is regulated by salt stress.

In an embodiment of the present disclosure, there is provided a method of heterologous expression of a gene of interest driven by a promoter as described herein, wherein said gene of interest expression is regulated by water and salt stress.

In an embodiment of the present disclosure, there is provided a method of heterologous expression of a gene of interest driven by a promoter as described herein, wherein said transformation is carried out by a method selected from the group consisting of *Agrobacterium* mediated transformation method, particle gun bombardment method, in planta transformation method, liposome mediated transformation method, protoplast transformation method, microinjection method, and macroinjection method.

In an embodiment of the present disclosure, there is provided a method of heterologous expression of a gene of interest driven by a promoter as described herein, wherein said transformation is *Agrobacterium* mediated transformation method.

In an embodiment of the present disclosure, there is provided a promoter as described herein, wherein said promoter is useful in heterologous expression of a gene of interest in a transgenic plant in a constitutive manner.

In an embodiment of the present disclosure, there is provided a promoter as described herein, wherein said promoter is useful in heterologous expression of a gene of interest in a transgenic plant in response to salt stress.

In an embodiment of the present disclosure, there is provided a promoter as described herein, wherein said promoter is useful in heterologous expression of a gene of interest in a transgenic plant in response to water stress.

In an embodiment of the present disclosure, there is provided a promoter as described herein, wherein said promoter is useful in heterologous expression of a gene of interest in a transgenic plant in response to water and salt stress.

In an embodiment of the present disclosure, there is provided a promoter as described herein, wherein said promoter activity is root specific in response to water stress.

In an embodiment of the present disclosure, there is provided a promoter as described herein for use in generating transgenic plants which heterologously express a gene of interest driven by said promoter.

In an embodiment of the present disclosure, there is provided DNA construct as described herein for use in generating transgenic plants which heterologously express a gene of interest driven by said promoter.

In an embodiment of the present disclosure, there is provided a DNA vector as described herein for use in generating transgenic plants which heterologously express a gene of interest driven by said promoter.

In an embodiment of the present disclosure, there is provided a recombinant host cell as described herein for use in generating transgenic plants which heterologously express a gene of interest driven by said promoter.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure.

Example 1

Plant Material and Growth Conditions

Mahyco parental line rice variety namely IR 58025 B was used and the seeds were stored at 28° C. It is an IIRI line and is publically available since 1990. The present invention can also be conducted with other publically available rice strains.

*Arabidopsis thaliana*, Ecotype: Columbia (col-0) seeds were used to generate plants. The seeds were stored at 25° C. The seeds are obtained in-house and the geographical origin of the seeds is in USA/Columbia.

Example 2

Isolation of DNA

*Gossypium hirsutum* probeset sequence ID Ghi.10553.1.S1_s_atgb|DN760229 was retrieved from PLEXdb (PLEXdb—plant expression database) experiment in search of stress induced genes for promoter isolation. Predicted mRNA sequence and putative promoter sequence of the above gene bank ID gb|DN760229 was retrieved from cottongen.org/gb/gbrowse/JGI_221_Dgenome and www-.cottongen.org/data/download/genome_JGI through CLC Genomics Workbench.

5' untranslated region (UTR) was isolated from the *Gossypium hirsutum* LTP (Lipid-transfer protein)/SSP (Seed storage protein) gene and coded as p2 (SEQ ID NO: 1). The forward primer having a nucleotide sequence as set forth in SEQ ID NO: 2 and reverse primer having a nucleotide sequence as set forth in SEQ ID NO: 3 were designed for amplification of the p2 promoter from cotton. PCR conditions used for amplification are given below in Table 1.

TABLE 1

| PCR step | Temperature (° C.) | Time (sec) | No. of cycles |
| --- | --- | --- | --- |
| Initial denaturation | 95 | 300 | 1 |
| Denaturation | 94 | 30 | 35 |
| Annealing | 55 | 30 | |
| Elongation | 72 | 120 | |
| Final elongation | 72 | 600 | |

Example 3

Construction of Vectors for Plant Transformation

Gateway cloning technology for directional cloning was used to clone p2 promoter. pENTR™/D-TOPO entry vector from Invitrogen™ was used to obtain p2 promoter entry clone. (Catalog number: K2400-20 pENTR™/D-TOPO® Cloning Kit, with One Shot® TOP10 Chemically Competent *E. coli*).

The amplified PCR product (SEQ ID NO: 1, 9 or 10) was cloned in a gateway entry vector PENTR/D-TOPO and recombined in pMDC164 gateway expression vector.

The TOPO® cloning reaction conditions used are provided below:

p2 PCR elute: 2 μl (20 ng/μl)
Salt solution: 0.5 μl
pENTR/D-TOPO: 0.5 μl (15-20 ng/μL linearized plasmid)
Total: 3 μl Transformation in Top10 One Shot® chemically competent *E. Coli* cells was performed as per the user guide.

LR recombination reaction was performed using pENTR p2 entry clone and pMDC164 gateway destination/expression vector. (pMDC 164 source: ABRC-abrc.osu.edu and Catalog number: 11791-020 for Gateway® LR Clonase® II Enzyme mix).

Figure 1:
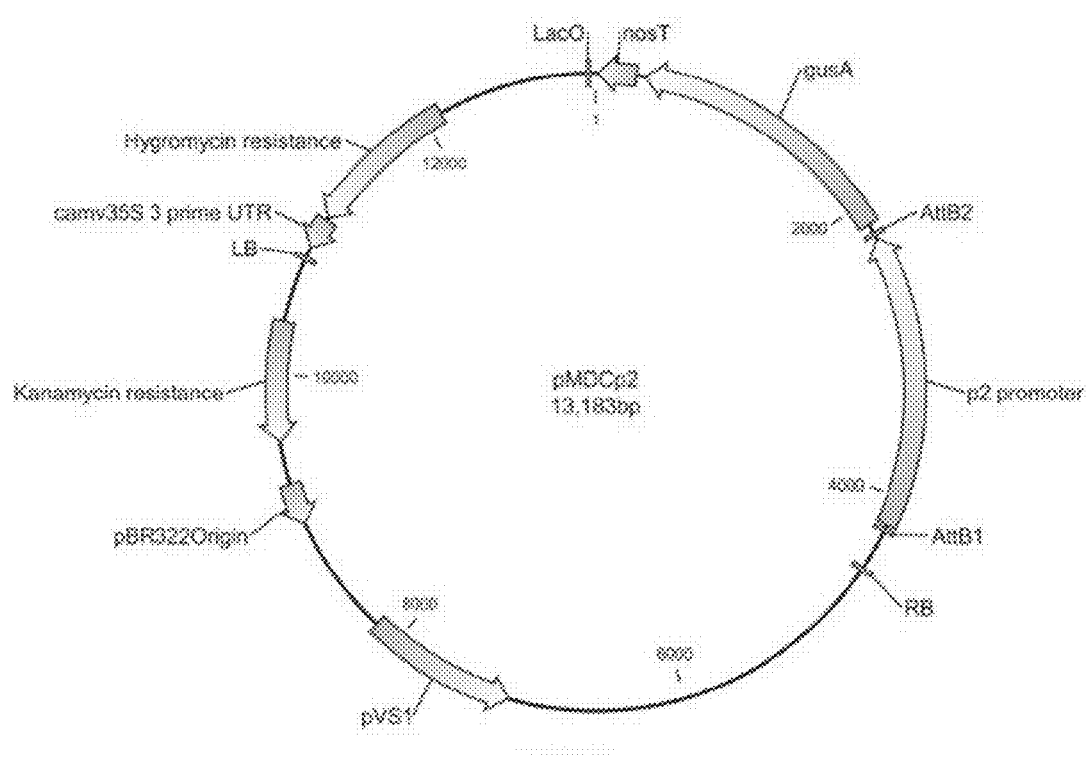
FIG. 1 depicts the expression vector map of pMDC p2, in accordance with an embodiment of the present disclosure.

LR Recombination Reaction:
pENTR p2: 1 μl (50 ng/μl)
LR clonase: 1 μl
PMDC 164: 1.5 μl (350 ng/μl)
Total: 3.5 μl Expression vector pMDC p2 (FIG. 1), pMDCp2Δ1 (FIG. 5A), or pMDCp2Δ2 (FIG. 5B) were mobilized in *Agrobacterium* strain EHA 105 (available in-house) by using freeze thaw method for plant transformation. In each case, approximately 1 μg of plasmid was added to 100 μl of EHA105 competent cells. The cells were then frozen in liquid nitrogen for 5 minutes and thawed at 370 C for 10 minutes. 1 ml of LB broth was added and incubated for 2-4 hrs at 28° C. Approximately 200 μL of bacterial culture was then spread on a pre-warmed selective plate and incubated at 280 C for 2 days.

Example 4

Transformation into *Agrobacterium*

*Arabidopsis* Transformation:

*Agrobacterium*-mediated transformation of *Arabidopsis thaliana* (Columbia-0) was performed using floral dip method as described in Das et al., 2011 with few modifications (Das et al., 2011, Advances in Bioscience and Biotechnology, 2, 59-67).

Growing of *Arabidopsis* Plants:

*Arabidopsis* seeds were kept for 3 days at 4° C. to break dormancy. Vernalized seeds were layered on soilrite, in plastic cups. Cups were watered periodically and incubated in growth chamber or in culture room at 25° C. for 16 hr light/8 hr dark condition up to inflorescence or floral stage comes up. Primary inflorescence was cut to obtain secondary buds.

Agrobacterium Culture Preparation:

Two days before the initiation of culture preparation, the floral dip Agrobacterium strain EHA 105 carrying pMDC164 p2-GUS was streaked on LB agar with antibiotic selection and incubated at 28° C. (chloramphenicol 10 mg/L and kanamycin 50 mg/L). Just before floral dip grown Agrobacterium culture scrapped from the plate, it was suspended in inoculum 3 media and ~1.0 OD at 600 nm (stationary phase) was used for infection.

Floral Dip:

Plants in the stage of budding were taken and dipped in the Agrobacterium culture by upturning for 40 to 50 seconds and by shaking in between. After floral dip plants were kept horizontally in tray cover with polythene bag for overnight at 25° C. in dark. Next day infected plants were kept upright and incubated at 25° C. for 16 hr. light/8 hr. dark in culture room up to seed harvesting.

Screening of Positive Transformants:

Arabidopsis $T_0$ seeds were kept for 3 days at 4° C. to break dormancy. Vernalized seeds were sterilized by 1.5% sodium hypochlrite for 1 minute then washed by D/W for 5 times and layered on 0.5×MS without sucrose and with 10 mg/L Hygromycin, incubated at 25° C. for 16 hr. light/8 hr dark in culture room.

Transformation efficiency was approximately 1% (not concentrated on transformation efficiency)

Media composition used are provided below:

1] Inoculum 3—MS salt: 0.5×, B5 vitamins: 1×, Glucose: 5%, BAP: 0.004M, Tween-20: 0.075% pH 5.7; 2] LB medium—10 g tryptone, 5 g yeast extract, 10 g NaCl per liter, Agar: 0.8% pH 7.0.

Rice Transformation:

Agrobacterium-mediated transformation of rice was performed by method as described in Hiei et al., 2006, Plant Cell, Tissue and Organ Culture. The transformation was performed with some modification in the method. For Agrobacterium-mediated transformation of rice PMS34-25B Mahyco parental line were used.

Freshly isolated immature embryos from plants grown in a green house, after 10-12 days post anthesis were inoculated with A. tumefaciens EHA105 pMDC164 p2. Three days before infection Agrobacterium strain EHA 105 carrying pMDC164 p2::GUS was streaked on LB agar with antibiotic selection and incubated at 28° C. (Chloramphenicol 10 mg/L and Kanamycin 50 mg/L). Just before infection grown Agrobacterium culture scrapped from plate, it was suspended in AA infection medium and ~1.0 OD at 600 nm (stationary phage) used for infection.

Seed Sterilization:

The seeds were de-husked by hand and sterilized in 70% ethanol for 30 seconds and in 1.5% sodium hypochlorite solution for 5 minutes. The immature seeds were rinsed several times in sterile water, and immature embryos of between 1.0 and 1.5 mm in length were collected under a stereoscopic dissection microscope. 5 µl of suspended Agrobacterium-culture dropped on scutellum of freshly isolated immature embryo incubated for 15 minutes then co-cultivated on NBAs medium for 4-6 days in dark at 25° C.

Resting Step:

After the co-cultivation, elongated shoots were removed from the immature embryos by a scalpel and the immature embryos were cultured on NBM medium that contained 250 mg/L cefotaxime and 100 mg/L carbenicillin with the scutellum-side up for 5 days.

Selection Step:

After resting step immature embryos were transferred on selection medium NBM with 250 mg/L cefotaxime and 50 mg 1/L hygromycin for 2 weeks followed by second selection of two weeks on the fresh NBM with 250 mg/L cefotaxime and 50 mg 1/L hygromycin medium.

Pre-Regeneration Step:

Callus clearly resistant to hygromycin derived from the scutella were transferred to a pre-regeneration medium NBPR that contained 40 mg/L hygromycin and 250 mg/L and cefotaxime and cultured for 10 days.

Regeneration Step:

Proliferating callus with green spots were cultured on an RNM regeneration medium that contained 30 mg/L hygromycin and 250 mg/L cefotaxime.

Rooting:

Regenerated plantlets were cultured on an MSN1.5 rooting medium that contained 30 mg/L hygromycin.

In all of the following steps, cultures were incubated at 28° C. under 16 hr. light and 8 hr. dark. The plants were hardened to soil in pots and grown to maturity in a greenhouse.

Media Composition

AA-infection: AA salts and amino acids (Toriyama and Hinata, 1985), B5 vitamins, 0.5 g/L, vitamin assay casamino acids, 20 g/l sucrose, 10 g/l D-glucose, 0.1 mM acetosyringone, pH 5.2.

NBM: N6 major salts, B5 minor salts and vitamins, 0.5 g/l vitamin assay casamino acids, 0.5 g/l L-proline, 0.3 g/L L-glutamine, 20 g/l D-maltose, 36 g/lD-mannitol, 2 mg/l 2,4-D, 1 mg/l NAA, 0.2 mg/l BA, 5 g/l Gelrite, pH 5.8.

NBPR: N6 major salts, B5 minor salts and vitamins, 0.5 g/L vitamin assay casamino acids, 0.5 g/L L-proline, 0.3 g/L L-glutamine, 30 g/L D-maltose, 2 mg/L 2,4-D, 1 mg/L 1 NAA, 1 mg/L BA, 7 g/L Gelrite, pH 5.8.

RNM: N6 major salts, B5 minor salts and vitamins, 0.3 g/L vitamin assay casamino acids, 0.3 g/L L-proline, 0.3 g/L L-glutamine, 30 g/L D-maltose, 1 mg/L NAA, 3 mg/L BA, 4 g/L agarose Type I, pH 5.8.

MSN1.5: Full strength of MS major salts, MS minor salts, MS vitamins and 100 mg/L myo-inositol, MS Cacl$_2$, MS iron, (Murashige and Skoog, 1962), 30 g/L sucrose, 1.5 mg/L NAA, 3 g/L phytagel, pH 5.8

Eight independent events were regenerated and three were selected for analysis. Transformation efficiency was 30%.

Cotton Transformation

Cotton cultivar used for transformation Coker 310FR ((Gossypium hirsutum). Cotton transformation protocol: Agrobacterium-mediated transformation of cotton was performed by method as described by Chaudhary et al. 2003 and Kumar et al. 1998 with some modification.

Seed Surface Sterilization:

Mature delinted seeds were sterilized by 100% ethanol for 2 minutes followed by 0.1% mercuric chloride treatment for 5 minutes.

Seed Inoculation:

Mature surface sterilized seeds blotted well and inoculated on SIM culture medium in bottles and incubated at 28° C. in three tube lights for 5 days.

SIM Culture Medium:

MS salts and vitamins, 3% sucrose, pH 5.8, 0.8% agar.

Agrobacterium Culture Preparation:

Agrobacterium strain EHA105 pMDCp2 was streaked from glycerol stock on solid LB medium supplemented with 10 mg/l of chloramphenicol and 50 mg/l of kanamycin and allowed to grow for 48 hrs. at 28° C. The suspension was prepared in liquid LB medium supplemented with 10 mg/l of chloramphenicol and 50 mg/l of kanamycine and allowed to grow for overnight at 28° C. The obtained O.D. (approximately 2.0 at 600 nm of wavelength) was diluted 20 times in liquid CTM1 culture medium (so that final O.D. reached to approximately 0.1). This diluted *Agrobacterium* suspension was used for transformation.

Infection:

0.5 cm long hypocotyl segments from 5 days old seedlings were used as explants for infection. Explants were soaked in *Agrobacterium* suspension for 20 minutes, blotted well and co-cultivated for 3 days at 22° C. on CTM1 culture medium supplemented with 100 μM of acetosyringone and covered with a layer of Whatman filter paper #1 to reduce the overgrowth of *Agrobacterium*.

After co-cultivation explants were washed in liquid CTM1 culture medium supplemented with 250 mg/l of carbenicillin, blotted well and transferred 5 explants in each glass petri-dish containing 70-80 ml of CTM1 culture medium supplemented with 10 mg/l of hygromycin and 250 mg/l of augmentin, IVIES 500 mg/L. Incubated for 5-6 wk at 28° C. in single tube light.

Friable callus from 3 individual explants was mulched in each glass petri-dish containing 70-80 ml of CTM2 culture medium supplemented with 7.5 mg/l of hygromycin and 100 mg/l of augmentin. Incubated at 28° C. in single tube light for 7-8 wk.

Well developed embryogenic calli were sub-cultured on 50 ml of CTM2 culture medium supplemented with 7.5 mg/l of hygromycin and 250 mg/l of carbenicillin, incubated for 2 wk at 28° C. in single tube light.

Regular subcultures of embryogenic calli (15 days each) on 50 ml of CTM3 culture medium incubated at 28° C. in three tube lights, last sub-cultured plates will be maintained for another 15 days as a back up and also to pick up the elongated embryos. Embryos were also sub-cultured on same medium (germinated embryos to ½ MSB solid culture medium).

Culture Media

CTM1 (liquid): MS salts and $B_5$ vitamins, glucose 3% (wt/vol), 0.1 mg/l of 2,4 D (sigma) and 0.5 mg/l of kinetin (Sigma), pH 5.9 (in this medium glucose was not filter sterilized).

CTM1: MS salts and $B_5$ vitamins, glucose 3% (wt/vol), 0.1 mg/l of 2,4 D (sigma) and 0.5 mg/l of kinetin (Sigma), 0.2% phytagel (Sigma), pH 5.9.

CTM2: MS salts and $B_5$ vitamins, glucose 3% (wt/vol), 0.2% phytagel (Sigma), pH 5.9.

CTM3: MS salts (1.9 g/l of $KNO_3$ additional) and $B_5$ vitamins, glucose 3% (wt/vol), 0.2% phytagel (Sigma), pH 5.9.

½ MSB (solid): ½ MS salts, $B_5$ vitamins, 1.5% (wt/vol) sucrose, pH 5.9, 0.2% (wt/vol) phytagel (sigma), ½ MSB (liquid): ½ MS salts, $B_5$ vitamins, 1.5% (wt/vol) sucrose, pH 5.9

In CTM1, CTM2 and CTM3 culture media, final volume of one liter culture medium without glucose was adjusted to 880 ml and autoclved. Glucose (30 g) was dissolved in 100 ml of distilled water, so that the final volume reached to 120 ml was filter sterilized and added to the autoclaved warm culture media.

Wherever augmentin was used in culture medium, it was mixed in required concentration with glucose solution, pH was adjusted to 5.9, it was filter sterilized and then added to the autoclaved warm culture medium.

From cotton transformation one independent event was generated and selected. Very less explants were used for transformation.

Example 5

GUS Assay

Stable GUS expression of p2 promoter (SEQ ID NO: 1) was performed in rice and cotton. Tissues were put in GUS buffer for over night then bleached in alcohol and checked for expression.

Figure 2:
FIG. 2 depicts the GUS expression pattern driven p2 promoter in rice and cotton, in accordance with an embodiment of the present disclosure.

The GUS buffer composition for 100 ml is provided below;

Potassium phosphate buffer (0.2M): 50 ml
Triton X-100 (0.1%): 10 ml
Potassium ferricyanide (50 mM): 2 ml
Potassium ferrocyanide (50 mM): 2 ml
Methanol: 20 ml
X-Gluc (50 mg/ml): 1 ml
D/W: 15 ml FIG. 2 depicts GUS expression driven by p2 promoter in rice and cotton. As seen in FIG. 2, qualitative stable GUS expression in p2 rice events pMDC p2-4 and pMDC p2-8 can be seen in different tissues like leaf, root, seed, lemma and palea in rice. In cotton, stable GUS expression in p2 cotton event CT/pMDC p2-1B can be seen in leaf and root tissues.

Figure 3:
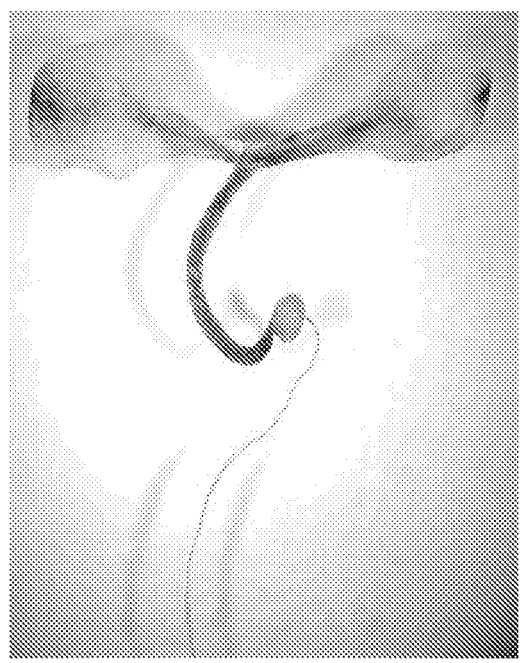
FIG. 3 depicts the GUS expression pattern driven by p2 promoter in *Arabidopsis* plant, in accordance with an embodiment of the present disclosure.

FIG. 3 shows the qualitative histochemical stable GUS expression in p2 *Arabidopsis* T1 plant pMDC p2-1-1, where strong expression particularly in roots can be observed compared to leaf and stem tissues. FIG. 8 shows the GUS expression in T3 plant.

As seen in FIG. 2, FIG. 3, and FIG. 8, it can be inferred that promoter p2 (SEQ ID NO: 1) drives expression of GUS in a constitutive and non-tissue specific manner, though root expression seems to be higher than in other tissues. Quantification of GUS activity was performed by fluorometric assay described in Jefferson et al., 1987 (Jefferson et al., 1987, EMBO J., 6, 3901-3907) and Gallagher, 1992 (Gallagher, S. R. (1992) Academic Press, Inc., New York, pp. 47-59).

Plant Tissue Extract:

100 mg leaf tissues were ground in 200 μl of extraction buffer in micro-centrifuge tube. The leaf tissue was then centrifuged at 12000 rpm for 15 minutes at 40 C to remove cell debris. Supernatant was transferred to a fresh tube.

MUG Assay:

20 μl of homogenates (approximately μg of protein) were mixed with 80 μl of GUS assay buffer. The mixture was vortex and incubated at 370 C for 30 minutes and 60 minutes water bath. 41 of each reaction mixture and of each MU standard were mixed with 475 μl of stop buffer. 200 μl from above step were loaded by duplicated manner in a microtiter plate and florescence were determined, excitation at 365 nm and emission at 444 nm).

Calculation of GUS Activity:

$$\text{pmoles MU/μg of protein/min} = \text{(pmoles of MU/well)} / 0.5 \text{ μg protein} \times \text{minute of the assay}$$

Composition of Buffers:

Extraction buffer: 50 mM NaPO4 pH 7.0, 10 mM EDTA, 0.1% Triton X-100, 0.1% sodium lauryl sarcosine, 10 mM β-mercaptoethanol. Store at 40° C.

GUS buffer assay: 2 mM MUG extraction buffer (10 ml assay solution mix MUG 8.8 mg in extraction buffer) was prepared freshly just before use.

Concentrated MU calibration stock solution: Mixed 9.9 mg in 50 ml D/W to prepare 1 mM MU stock. 1:10 dilution was prepared to obtain 100 μM MU stock and 1:50 dilution to obtain 20 μM stock solution.

For standard curve following dilutions were used: 0, 4, 8, 12, 20, 40, 100, 250, and 500 pmol MU.

Stop buffer: 200 mM Na2CO3 pH 11.2 (21.2 gm/L).

The assay was performed on transgenic leaf tissues. Table 2 shows rice p2-8A event (leaf tissue) GUS MU quantification results.

TABLE 2

| | | Concentrations | | |
|---|---|---|---|---|
| S. No. | Sample | pmoles/well | pmoles MU/μg protein/min | Standard Error |
| 1 | Wild Type | 0.26184 | 1.7456 | 0.2635 |
| 2 | Empty GUS | 3.1583 | 21.0553 | 4.57 |
| 3 | p2::GUS | 452.28 | 3015.2 | 120.01 |
| 4 | 35S::GUS | 750 | 5000 | 117.87 |

Along with 2 clones of p2-8 event (p2-8A and p2-8B) p2-4 and p2-6 events from rice and one event from cotton CT/pMDC p2-1B (which are PCR positive for presence of p2 promoter and qualitative histochemical GUS positive) are screened for quantitative GUS expression.

Among three events of rice p2-8 showed the best expression and cotton event also showed the GUS quantification value near to the p2-8 event.

Quantification values in pMoles MU/μg protein/min: Wild Type (1.7456), Empty GUS (21.0553), Rice events—p2-8A (3015.2), p2-4B (185.33), p2-6B (61.97), Cotton event—p2-1B (2484.5) and 35S::GUS (5000).

Figure 4:
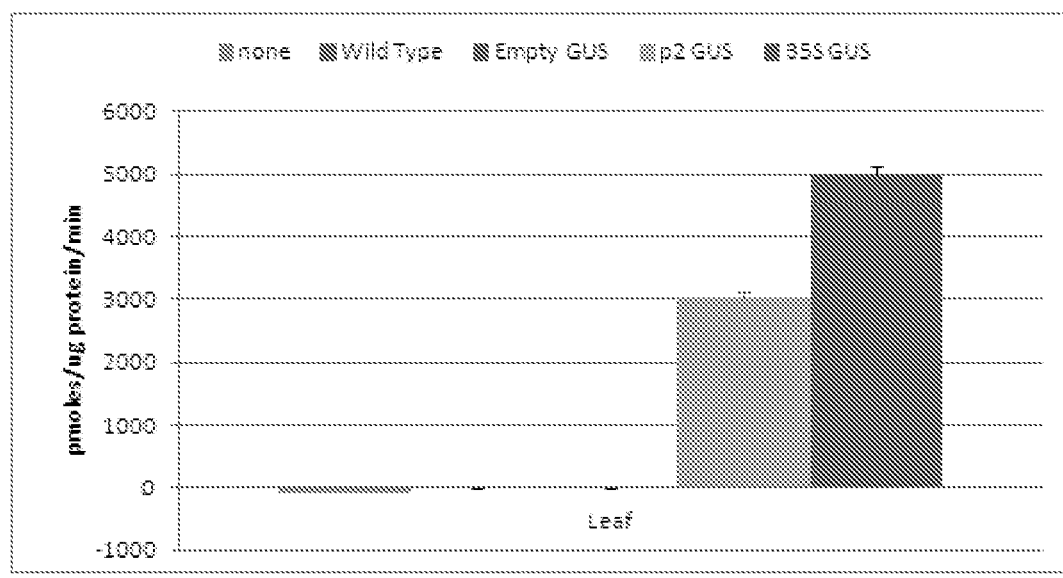
FIG. 4 depicts the GUS quantification in rice driven by p2 or 35S promoter, in accordance with an embodiment of the present disclosure.

FIG. 4 depicts the graphical representation of the data as provided above in Table 2. As seen from Table 2, and FIG. 4, it can be inferred that promoter p2 (SEQ ID NO: 1) can drive expression of GUS up to 60% that of GUS expression levels driven by the constitutive promoter 35S.

Example 6

Analysis of Promoter by Plant Cis-Acting Regulatory DNA Elements (PLACE) Database PLACE analysis provides information on Cis-regulatory element present in p2 promoter. Motifs involved in abiotic stress response, transcription factor binding sites, tissue specificity are present in the p2 promoter were studied through deletion analysis to get desired activity of the promoter.

Analysis of the p2 promoter fragment (SEQ ID NO: 1) using PLACE database identified various stress responsive and tissue specific motifs in the p2 promoter sequence. [Higo K et al., 1999, Nucleic Acids Res.; 27(1):297-300; Omodele et al., 2010, Computational Biology and Chemistry 34, 268-283.] Table 3 below provides a list of motifs identified in the p2 promoter.

TABLE 3

List of motifs identified in the p2 promoter.

| S. No. | Motifs | Sequence | Function |
|---|---|---|---|
| 1. | -300 ELEMENT | TGCAAAAG | Seed storage protein deposition-endosperm expression |
| 2. | ABRELATERD1 | ACGTG | Confers dehydration |
| 3. | ACGTABOX | TACGTA | Binding of bZIP TF |
| 4. | ACGTATERD1 | ACGT | Confers dehydration |
| 5. | AMYBOX2 | TATCCAT | alpha-amylase Amy3D expression during sugar starvation |
| 6. | ANAERO2CONSENSUS | AGCAGC | Fermentative pathway |
| 7. | ARFAT | TGTCTC | Binding site for auxin response factor |
| 8. | ARR1AT | AGATT | ARR1-binding element operate as transcriptional activators |
| 9. | ASF1MOTIFCAMV | TGACG | Defense response element |
| 10. | BIHD1OS | TGTCA | Transcriptional factor involved in disease resistance responses |
| 11. | BOXIINTPATPB | ATAGAA | Transcription initiation |
| 12. | BOXLCOREDCPAL | ACCTTCC | Transcriptional activator of the phenylalanine ammonia-lyase gene |
| 13. | CAATBOX1 | CAAT | Confers tissue specificity |
| 14. | CACTFTPPCA1 | TACT, CACT | Mesophyll-specific gene expression in the C4 plant |
| 15. | CARGNCAT | SEQ ID NO: 5 | Regulates expression of a gene encoding an enzyme involved in gibberellin metabolism. |
| 16. | CARGCW8GAT | SEQ ID NO: 6 | Binding site selection for the plant MADS domain protein AGL15 |

TABLE 3-continued

List of motifs identified in the p2 promoter.
Table 3:

| S. No. | Motifs | Sequence | Function |
|---|---|---|---|
| 17. | CCA1ATLHCB1 | AACAATCT | A myb-related transcription factor is involved in the phytochrome regulation of an *Arabidopsis* Lhcb gene |
| 18. | CCAATBOX1 | CCAAT | Confers tissue specificity |
| 19. | CIACADIANLELHC | SEQ ID NO: 7 | Circadian expression |
| 20. | CURECORECR | GTAC | Core of a CuRE (copper-response element) involved in oxygen-response |
| 21. | DOFCOREZM | AAAG | Transcription factors are involved in carbon metabolism |
| 22. | DPBFCOREDCDC3 | ACACAAG/ ACACCCG | Tissue specificity |
| 23. | EBOXBNNAPA | CAAGTG/ CATGTG/ CAAATG/ CAGCTG/ CACCTG/ CAATTG | Tissue specificity |
| 24. | EECCRCAH1 | GACTTTC/ GATTTGC/ GATTTGC | Binding site of Myb transcription factor |
| 25. | ELRECOREPCRP1 | TTGACC | Elicitor Responsive Element |
| 26. | GATABOX | GATA | Tissue specificity |
| 27. | GT1CONSENSUS | GATAAT/ GAAAAT/ GATAAA/ GAAAAA | Salt tolerance and pathogenesis interaction |
| 28. | GT1CORE | GGTTAA | Salt tolerance and pathogenesis interaction |
| 29. | GT1GMSCAM4 | GAAAAA | Salt tolerance and pathogenesis interaction |
| 30. | GTGANTG10 | GTGA | Pollen specific expression |
| 31. | HDZIP2ATATHB2 | TAATAATTA | Transcription factor signals in Plant morphogenesis |
| 32. | IBOXCORE | GATAA | Conserved sequence upstream of light-regulated genes |
| 33. | INRNTPSADB | CTCATTTC | Initiator elements |
| 34. | LECPLEACS2 | TAAAATAT | Defense response |
| 35. | MYBST1, | TAACCA | Dehydration responsive element |
| 36. | MYCATERD1 | CATGTG | Confers tissue specificity |
| 37. | MYCCONSENSUSAT | CAAGTG/ CATGTG/ CAGCTG | Confers tissue specificity |
| 38. | NODCON1GM | AAAGAT | Nodule specific |
| 39. | NODCON2GM | CTCTT | Nodule specific |
| 40. | NTBBF1ARROLB, | ACTTTA | Tissue specificity |

TABLE 3-continued

List of motifs identified in the p2 promoter.
Table 3:

| S. No. | Motifs | Sequence | Function |
|---|---|---|---|
| 41 | OSE1ROOTNODULE | AAAGAT | Organ specific element |
| 42. | P1BS | GAATATAC | Phosphate starvation response |
| 43. | POLASIG1 | AATAAA | Plant specific poly (A) signals |
| 44. | POLLEN1LELAT52, | AGAAA | Pollen specific activation |
| 45. | PREATPRODH | ACTCAT | Hypoosmolarity-responsive element |
| 46. | PRECONSCRHSP70A | SEQ ID NO: 8 | Plastid response element that acts as an enhancer |
| 47. | RAV1AAT | CAACA | Tissue specificity |
| 48. | RBCSCONSENSUS | AATCCAA | Expression of genes encoding ribulose-1,5-bisphosphate carboxylase |
| 49. | ROOTMOTIFTAPOX1 | ATATT | Tissue specificity |
| 50. | RYREPEATBNNAPA | CATGCA | Seed specific expression |
| 51. | S1FBOXSORPS1L21 | ATGGTA | Encoding ribosomal protein |
| 52. | S1FSORPL21 | ATGGTATT | Encoding plastid ribosomal protein |
| 53. | SEF4MOTIFGM7S | ATTTTTG | Seed storage protein |
| 54. | SORLIP1AT | GCCAC | Tissue specificity |
| 55. | SURE2STPAT21 | AATACTAAT | Direct metabolic and developmental regulation of storage protein gene |
| 56. | SURECOREATSULTR11 | GAGAC | Sulfur deficiency response |
| 57. | TAAAGSTKST1 | TAAAG | Guard cell-specific gene expression |
| 58. | TATABOX2 | TATAAAT | Accurate initiation |
| 59. | TATABOX3 | TATTAAT | Accurate initiation |
| 60. | TATABOX5 | TTATTT | Accurate initiation |
| 61. | TATABOXOSPAL | TATTTAA | DNA binding element |
| 62. | TATCCAOSAMY | TATCCA | Sugar and hormone regulation |
| 63. | TATCCAYMOTIFOSRAMY3D | TATCCAT | Sugar repression |
| 64. | TBOXATGAPB | ACTTTG | Modulators of light-activated transcription |
| 65. | TGACGTVMAMY | TGACGT | Seed specific expression |
| 66. | WBOXATNPR1 | TTTGACC | Transcriptional factor involved in environmental stresses |
| 67. | WBOXHVISO1 | TGACT | Sugar-responsive elements |
| 68. | WBOXNTERF3 | TGACC/ TGACT | Defense response |
| 69. | WRKY71OS | TGAC | Salt tolerance and pathogenesis interaction |

"/" in the Sequence column represents a break between distinct sequences that represents an alternate but distinct sequence that gives rise to the consensus sequence under the heading in column 2 of Table 3.

Example 7

Deletion Analysis of Promoter p2

In order to further characterize the promoter p2 activity, deletion analysis was carried out. 2 different deletion constructs were prepared, namely, p2Δ1 (SEQ ID NO: 9), and p2Δ2 (SEQ ID NO: 10). Two deletion promoters have been cloned in pMDC expression vector, mobilized in EHA 105 *Agrobacterium* strain (EHA pMDC p2 Δ1 And EHA pMDC p2 Δ2) for plant transformation. The promoter sequences were earlier confirmed by sequencing.

The PCR conditions used to produce the fragment of p2Δ1 are as given below in Table 4. The forward and reverse primer set used to amplify SEQ ID NO: 9 are as set forth in SEQ ID NO: 11, and SEQ ID NO: 12 respectively.

TABLE 4

| PCR step | Temperature (° C.) | Time (sec) | No. of cycles |
|---|---|---|---|
| Initial denaturation | 95 | 300 | 1 |
| Denaturation | 94 | 30 | 40 |
| Annealing | 51 | 30 | |
| Elongation | 72 | 20 | |
| Final elongation | 72 | 600 | |

The PCR conditions used to produce the fragment of p2Δ2 are as given below in Table 5. The forward and reverse primer set used to amplify SEQ ID NO: 10 are as set forth in SEQ ID NO: 13, and SEQ ID NO: 14 respectively.

TABLE 5

| PCR step | Temperature (° C.) | Time (sec) | No. of cycles |
|---|---|---|---|
| Initial denaturation | 95 | 300 | 1 |
| Denaturation | 94 | 30 | 40 |
| Annealing | 50 | 30 | |
| Elongation | 72 | 60 | |
| Final elongation | 72 | 600 | |

Table 6 below depicts the cis-regulatory motif analysis (PLACE) of p2Δ1 deletion fragment.

TABLE 6

| Sr. No. | Factor or Site Name | Loc. | Signal Sequence | Function |
|---|---|---|---|---|
| 1 | GTGANTG10 | 5 (+) | GTGA | Pollen specific |
| 2 | SURECOREATSULTR11 | 7 (+) | GAGAC | Core of sulfur-responsive element |
| 3 | CAATBOX1 | 27 (+) | CAAT | Sequences responsible for the tissue specific promoter activity of a pea legumin gene in tobacco |
| 4 | POLASIG3 | 28 (+) | AATAAT | Plant polyA signal |
| 5 | RAV1AAT | 36 (+) | CAACA | Binding consensus sequence of *Arabidopsis* transcription factor, RAV1/The expression level of RAV1 were relatively high in rosette leaves and roots |
| 6 | DPBFCOREDCDC3 | 38 (+) | ACACNNG | A novel class of bZIP transcription factors, DPBF-1 and 2 (Dc3 promoter-binding factor-1 and 2) binding core sequence; Found in the carrot (D.c.) Dc3 gene promoter; Dc3 expression is normally embryo-specific, and also can be induced by ABA |
| 7 | LTRECOREATCOR15 | 42 (+) | CCGAC | Core of low temperature responsive element (LTRE) of cor15a gene in *Arabidopsis*/A portion of repeat-C (C-repeat), TGGCCGAC, which is repeated twice in cor15a promoter. |
| 8 | PRECONSCRHSP70A | 42 (+) | SCGAYNRNNNNNNNNNNNNNNNHD | Consensus sequence of PRE (plastid response element) in the promoters of HSP70A in *Chlamydomonas*; Involved in induction of HSP70A gene by both MgProto and light. |
| 9 | DOFCOREZM | 54 (+) | AAAG | Core site required for binding of Dof proteins in maize/Four cDNAs encoding Dof proteins, Dof1, Dof2, Dof3 and PBF, have been isolated from maize; PBF is an endosperm specific Dof protein that binds to prolamin box |

TABLE 6-continued

| Sr. No. | Factor or Site Name | Loc. | Signal Sequence | Function |
|---|---|---|---|---|
| 10 | CACTFTPPCA1 | 78 (+) | YACT | Mesophyll expression module 1/ found in the cis-regulatory element in the distal region of the phosphoenolpyruvate carboxylase (ppcA1) of the C4 dicot |
| 11 | MYBPLANT | 85 (+) | MACCWAMC | Plant MYB binding site |
| 12 | INRNTPSADB | 102 (+) | YTCANTYY | "Inr (initiator)" elements found in the tobacco psaDb gene promoter without TATA boxes; Light-responsive transcription of psaDb depends on Inr, but not TATA box; |
| 13 | TATABOX2 | 112 (+) | TATAAAT | "TATA box"; TATA box found in the 5'upstream region of pea legA gene; sporamin A of sweet potato; TATA box found in beta-phaseolin promoter (Grace et al.); sequence and spacing of TATA box elements are critical for accurate initiation. |
| 14 | CCA1ATLHCB1 | 119 (+) | AAMAATCT | CCA1 binding site; CCA1 protein (myb-related transcription factor) interact with two imperfect repeats of AAMAATCT in Lhcb1*3 gene of *Arabidopsis thaliana* Related to regulation by phytochrome. |
| 15 | CAATBOX1 | 121 (+) | CAAT | CAAT promoter consensus sequence" found in legA gene of pea; CAAT; legA; seed; pea (*Pisum sativum*) Shirsat A, Wilford N, Croy R, Boulter D Sequences responsible for the tissue specific promoter activity of a pea legumin gene in tobacco |
| 16 | SORLIP1AT | 138 (+) | GCCAC | one of "Sequences Over-Represented in Light-Induced Promoters (SORLIPs) in *Arabidopsis* |
| 17 | DOFCOREZM | 152 (+) | AAAG | Core site required for binding of Dof proteins in maize (Z.m.); Dof proteins are DNA binding proteins, with presumably only one zinc finger, and are unique to plants |

Table 7 below depicts the cis-regulatory motif analysis (PLACE) of p2Δ2 deletion fragment.

TABLE 7

| Sr. No. | Factor or Site Name | Loc. | Signal Sequence | Function |
|---|---|---|---|---|
| 1 | RYREPEATBNNAPA | 8(+) | CATGCA | "RY repeat" found in RY/G box (the complex containing the two RY repeats and the G-box) of napA gene in *Brassica napus* (B.n.); Found between -78 and -50; Required for seed specific expression; |
| 2 | DOFCOREZM | 24(+), 29(+), 149(+), 384(+), 480(+), | AAAG | Core site required for binding of Dof proteins in maize/Four cDNAs encoding Dof proteins, Dof1, Dof2, Dof3 and PBF, have been isolated from maize; |

TABLE 7-continued

| Sr. No. | Factor or Site Name | Loc. | Signal Sequence | Function |
|---|---|---|---|---|
| | | 514(+), 587(+), 592(+), 626(+), 675(+), 773(+) | | PBF is an endosperm specific Dof protein that binds to prolamin box |
| 3 | POLLEN1LEL AT52 | 26(+), 478(+), 589(+) | AGAAA | One of two co-dependent regulatory elements responsible for pollen specific activation of tomato (L.e.) lat52 gene |
| 4 | MYBST1 | 32(+) | GGATA | Core motif of MybSt1 (a potato MYB homolog) binding site; MybSt1 cDNA clone was isolated by using CaMV 35S promoter domain A as a probe (Baranowskij et al. 1994) |
| 5 | GATABOX | 33(+), 107(+), 279(+), 411(+), 552(+) 560(+) | GATA | "GATA box"; GATA motif in CaMV 35S promoter; Binding with ASF-2; Three GATA box repeats were found in the promoter of Petunia (P.h.) chlorophyll a/b binding protein, Cab22 gene; Required for high level, light regulated, and tissue specific expression; Conserved in the promoter of all LHCII type I Cab genes; |
| 6 | GT1CONSENSUS | 33(+), 279(+), 524(+), 560(+) | GRWAAW | Consensus GT-1 binding site in many light-regulated genes, e.g., RBCS from many species, PHYA from oat and rice, spinach RCA and PETA, and bean CHS15; R = A/G; W = A/T; For a compilation of related GT elements and factors, see Villain et al. (1996); GT-1 can stabilize the TFIIA-TBP-DNA (TATA box) complex; The activation mechanism of GT-1 may be achieved through direct interaction between TFIIA and GT-1; Binding of GT-1-like factors to the PR-1a Promoter influences the level of SA-inducible gene expression. |
| 7 | IBOXCORE | 33(+), 107(+), 279(+), 560(+) | GATAA | "I box"; "I-box"; Conserved sequence upstream of light-regulated genes of both monocots and dicots; |
| 8 | ASF1MOTIFC AMV | 57(+) | TGACG | "ASF-1 binding site" in CaMV 35S promoter; ASF-1 binds to two TGACG motifs; (AS1); Found in HBP-1 binding site of wheat histone H3 gene; TGACG motifs are found in many promoters and are involved in transcriptional activation of several genes by auxin and/or salicylic acid |
| 9 | TGACGTVMA MY | 57(+) | TGACGT | "TGACGT motif" found in the Vigna mungo (V.m.) alpha-Amylase (Amy) gene promoter; Located between −128 and −123; Required for high level expression of alpha-Amylase in the cotyledons of the germinated seeds; |
| 10 | WRKY71OS | 57(+), 318(+) | TGAC | "A core of TGAC-containing W-box" of, e.g., Amy32b promoter; Binding site of rice WRKY71, a transcriptional repressor of the gibberellins signaling pathway; |

TABLE 7-continued

| Sr. No. | Factor or Site Name | Loc. | Signal Sequence | Function |
|---|---|---|---|---|
| | | | | Parsley WRKY proteins bind specifically to TGAC-containing W box elements within the Pathogenesis-Related Class10 (PR-10) genes (Eulgem et al., 1999) |
| 11 | ABRELATERD1 | 59(+) | ACGTG | ABRE-like sequence (from -199 to -195) required for etiolation-induced expression of erd1 (early responsive to dehydration) in Arabidopsis; |
| 12 | ACGTATERD1 | 59(+), 201(+), 449(+), 555(+) | ACGT | ACGT sequence (from -155 to -152) required for etiolation-induced expression of erd1 (early responsive to dehydration) in Arabidopsis |
| 13 | MYBCORE | 68(+) | CNGTTR | Binding site for all animal MYB and at least two plant MYB proteins ATMYB1 and ATMYB2, both isolated from Arabidopsis; ATMYB2 is involved in regulation of genes that are responsive to water stress in Arabidopsis; A petunia MYB protein (MYB.Ph3) is involved in regulation of flavonoid biosynthesis (Solano et al.) |
| 14 | CACTFTPPCA1 | 80(+), 169(+), 307(+), 417(+), 699(+) | YACT | Mesophyll expression module 1/ found in the cis-regulatory element in the distal region of the phosphoenolpyruvate carboxylase (ppcA1) of the C4 dicot |
| 15 | HDZIP2ATATHB2 | 83(+) | TAATMATTA | Binding site of the Arabidopsis (A.T.) homeobox gene (ATHB-2) found in its own promoter; Located between -72 and -80; Similar to the HD-ZIP-2 binding consensus sequence; ATHB-2 is regulated by light signals which function as a negative autoregulator of its own gene; M = C/A; |
| 16 | POLASIG3 | 84(+), 423(+), 649(+) | AATAAT | "Plant polyA signal"; Consensus sequence for plant |
| 17 | ROOTMOTIFTAPOX1 | 92(+), 206(+), 259(+), 269(+), 298(+), 333(+), 364(+), 412(+), 506(+) | ATATT | Motif found both in promoters of rolD; Elmayan T, Tepfer M Evaluation in tobacco of the organ specificity and strength of the rolD promoter, domain A of the 35S promoter and the 35S^2 promoter Transgenic Res 4:388-396 (1995) |
| 18 | INRNTPSADB | 97(+), 723(+) | YTCANTYY | Inr (initiator)" elements found in the tobacco psaDb gene promoter without TATA boxes; Light-responsive transcription of psaDb depends on Inr, but not TATA box. |
| 19 | CAATBOX1 | 99(+), 400(+), 499(+), 648(+), 742(+) | CAAT | Sequences responsible for the tissue specific promoter activity of a pea legumin gene in tobacco |
| 20 | POLASIG1 | 117(+), 188(+), 264(+), 484(+) | AATAAA | "PolyA signal"; poly A signal found in legA gene of pea, rice alpha-amylase; -10 to -30 in the case of animal genes. Near upstream elements (NUE) in Arabidopsis (Loke et al. 2005) |

TABLE 7-continued

| Sr. No. | Factor or Site Name | Loc. | Signal Sequence | Function |
|---|---|---|---|---|
| 21 | EBOXBNNAPA | 175(+), 499(+) | CANNTG | E-box of napA storage-protein gene of *Brassica napus* |
| 22 | MYCCONSENSUSAT | 175(+), 499(+) | CANNTG | MYC recognition site found in the promoters of the dehydration-responsive gene rd22 and many other genes in *Arabidopsis*; Binding site of ATMYC2/MYC recognition sequence in CBF3 promoter; Binding site of ICE1 (inducer of CBF expression 1) that regulates the transcription of CBF/DREB1 genes in the cold in *Arabidopsis*; ICE1 (Chinnusamy et al., 2004);) |
| 23 | GTGANTG10 | 178(+), 545(+) | GTGA | "GTGA motif" found in the promoter of the tobacco (N.t.) late pollen gene g10 which shows homology to pectate lyase and is the putative homologue of the tomato gene lat56; Located between -96 and -93 |
| 24 | ACGTABOX | 200(+) | TACGTA | "A-box" according to the nomenclature of ACGT elements by Foster et al. (FASEB J 8:192-200 (1994)); One of ACGT elements; Found in ocs gene; RITA-1 binding site (Izawa et al. 1994); "G motif" by Toyofuku et al. (1998); G motif and TATCCAY motif (a GATA motif as its antisense sequence; are responsible for sugar repression (Toyofuku et al. 1998) |
| 25 | SEF4MOTIFGM75 | 228(+) | | "SEF4 binding site"; Soybean (G.m.) consensus sequence found in 5'upstream region (-199) of beta-conglycinin (7S globulin) gene (Gmg17.1); "Binding with SEF4 (soybean embryo factor 4)"; R = A/G; soybean; seed; storage protein; 7S; globulin; beta-conglycinin; |
| 26 | ARR1AT | 233(+), 238(+), 433(+), 519(+), 567(+), 572(+), 602(+) | NGATT | "ARR1-binding element" found in *Arabidopsis*; ARR1 is a response regulator; N = G/A/C/T; AGATT is found in the promoter of rice non-symbiotic haemoglobin-2 (NSHB) gene (Ross et al., 2004) |
| 27 | TATABOX5 | 242(+), 428(+) | TTATTT | "TATA box"; TATA box found in the 5'upstream region of pea (*Pisum sativum*) glutamine synthetase gene; a functional TATA element by in vivo analysis |
| 28 | TATABOXOSPAL | 243(+), 270(+) | TATTTAA | Binding site for OsTBP2, found in the promoter of rice pal gene encoding phenylalanine ammonia-lyase; OsTFIIB stimulated the DNA binding and bending activities of OsTBP2 and synergistically enhanced OsTBP2-mediated transcription from the pal promoter |
| 29 | S1FBOXSORPS1L21 | 252(+) | ATGGTA | "S1F box" conserved both in spinach (S.o.) RPS1 and RPL21 genes encoding the plastid ribosomal protein S1 and L21, respectively; Negative element; Might play a role in down regulating RPS1 and RPL21 promoter activity (Lagrange et al., 1993); |

TABLE 7-continued

| Sr. No. | Factor or Site Name | Loc. | Signal Sequence | Function |
|---|---|---|---|---|
| 30 | TATABOX3 | 260(+), 299(+), 334(+), 365(+) | TATTAAT | "TATA box"; TATA box found in the 5'upstream region of sweet potato sporamin A gene |
| 31 | PRECONSCRH SP70A | 277 9+), 663(+) | SCGAYN RNNNNN NNNNNN NNNNHD | Consensus sequence of PRE (plastid response element) in the promoters of HSP70A in Chlamydomonas; Involved in induction of HSP70A gene by both MgProto and light. |
| 32 | NTBBF1ARRO LB | 308(+) | ACTTTA | NtBBF1(Dof protein from tobacco) binding site in Agrobacterium rhizogenes (A.r.) rolB gene; Found in regulatory domain B (-341 to -306); Required for tissue-specific expression and auxin induction; rolB; Dof; auxin; domain B; root; shoot; meristem; vascular; |
| 33 | WBOXATNPR 1 | 317(+) | TTGAC | "W-box" found in promoter of Arabidopsis thaliana (A.t.) NPR1 gene; Located between +70 and +79 in tandem; They were recognized specifically by salicylic acid (SA)-induced WRKY DNA binding proteins; |
| 34 | CURECORECR | 341(+) | GTAC | GTAC is the core of a CuRE (copper-response element) found in Cyc6 and Cpx1 genes in Chlamydomonas; Also involved in oxygen-response of these genes; |
| 35 | CARGNCAT | 344(+) | CCWWW WWWWW GG | Noncanonical CArG motif (CC-Wx8-GG) found in the promoter region of DTA1 (AtGA2ox6); A relevant cis element for the response to AGL15 (AGAMOUS-like 15) in vivo/The embryo MADS domain protein AGAMOUS-Like 15 directly regulates expression of a gene encoding an enzyme involved in gibberellin metabolism. Plant Cell 16:1206-1219 (2004 |
| 36 | CARGCW8GA T | 345(+) | CWWWW WWWWG | A variant of CArG motif with a longer A/T-rich core; Binding site for AGL15 (AGAMOUS-like 15); W = A/T; CArG; AGL15; AGAMOUS; MADS; Arabidopsis thaliana Tang W, Perry SE.Binding site selection for the plant MADS domain protein AGL15: an in vitro and in vivo study. J Biol Chem.278:28154-28159 (2003) |
| 37 | LECPLEACS2 | 360(+) | TAAAAT AT | Core element in LeCp (tomato Cys protease) binding cis-element (from -715 to -675) in LeAcs2 gene; cysteine protease; ethylene; xylanase; ACS; Lycopersicon esculentum (tomato) Matarasso N, Schuster S, Avni A. A novel plant cysteine protease has a dual function as a regulator of 1-aminocyclopropane-1-carboxylic Acid synthase gene expression. Plant Cell. 17:1205-1216. (2005) |

TABLE 7-continued

| Sr. No. | Factor or Site Name | Loc. | Signal Sequence | Function |
|---|---|---|---|---|
| 38 | TATABOX2 | 374(+), 733(+) | TATAAAT | "TATA box"; TATA box found in the 5'upstream region of pea legA gene; sporamin A of sweet potato; TATA box found in beta-phaseolin promoter (Grace et al.); sequence and spacing of TATA box elements are critical for accurate initiation |
| 39 | TAAAGSTKST1 | 383(+) | TAAAG | TAAAG motif found in promoter of Solanum tuberosum (S.t.) KST1 gene; Target site for trans-acting StDof1 protein controlling guard cell-specific gene expression; KST1 gene encodes a K+ influx channel of guard cells |
| 40 | AMYBOX2 | 452(+) | TATCCAT | "amylase box"; "amylase element"; Conserved sequence found in 5'upstream region of alpha-amylase gene of rice, wheat, barley; "amylase box" (Huang et al. 1990); "amylase element" (Hwang et al., 1998);Three cis-elements required for rice alpha-amylase Amy3D expression during sugar starvation Plant Mol Biol 36:331-341 (1998) |
| 41 | TATCCAYMOTIFOSRAMY3D | 452(+) | TATCCAY | "TATCCAY motif" found in rice (O.s.) RAmy3D alpha-amylase gene promoter; Y = T/C; a GATA motif as its antisense sequence; TATCCAY motif and G motif are responsible for sugar repression (Toyofuku et al. 1998); |
| 42 | TATCCAOSAMY | 452(+) | TATCCA | "TATCCA" element found in alpha-amylase promoters of rice (O.s.)at positions ca.90 to 150 bp upstream of the transcription start sites; Binding sites of OsMYBS1, OsMYBS2 and OsMYBS3 which mediate sugar and hormone regulation of alpha-amylase gene expression; |
| 43 | MYB1AT | 490(+) | WAACCA | MYB recognition site found in the promoters of the dehydration-responsive gene rd22 and many other genes in Arabidopsis; W = A/T; |
| 44 | -300ELEMENT | 510(+) | TGHAAARK | Present upstream of the promoter from the B-hordein gene of barley and the alpha-gliadin, gamma-gliadin, and low molecular weight glutenin genes of wheat |
| 45 | NODCON1GM | 514(+) | AAAGAT | One of two putative nodulin consensus sequences; (NODCON2GM); nodulin Glycine max (soybean) Sandal NN, Bojsen K, Marcker KA.A small family of nodule specific genes from soybean. Nucleic Acids Res. 15:1507-1519 (1987). |
| 46 | OSE1ROOTNODULE | 514(+) | AAAGAT | One of the consensus sequence motifs of organ-specific elements (OSE) characteristic of the promoters activated in infected cells of root nodules |
| 47 | BIHD1OS | 538(+) | TGTCA | Binding site of OsBIHD1, a rice BELL homeo- domain transcription factor; HD; homeodomain; Oryza sativa (rice) Luo H, |

TABLE 7-continued

| Sr. No. | Factor or Site Name | Loc. | Signal Sequence | Function |
|---|---|---|---|---|
| | | | | Song F, Goodman RM, Zheng Z. Up-regulation of OsBIHD1, a rice gene encoding BELL homeodomain transcriptional factor, in disease resistance responses. Plant Biol (Stuttg). 7:459-468 (2005). |
| 48 | EECCRCAH1 | 603(+) | GANTTNC | "EEC"; Consensus motif of the two enhancer elements, EE-1 and EE-2, both found in the promoter region of the Chlamydomonas Cah1 (encoding a periplasmic carbonic anhydrase); Binding site of Myb transcription factor LCR1 (see Yoshioka et al, 2004); N = A/G/C/T; |
| 49 | SORLIP1AT | 608(+) 759(+) | GCCAC | one of "Sequences Over-Represented in Light-Induced Promoters (SORLIPs) in Arabidopsis |
| 50 | SURECOREAT SULTR11 | 628(+) | GAGAC | Core of sulfur-responsive element (SURE) found in the promoter of SULTR1;1 high-affinity sulfate transporter gene in Arabidopsis |
| 51 | RAV1AAT | 657(+) | CAACA | Binding consensus sequence of Arabidopsis transcription factor, RAV1/The expression level of RAV1 were relatively high in rosette leaves and roots. |
| 52 | DPBFCOREDCDC3 | 659(+) | ACACNNG | A novel class of bZIP transcription factors, DPBF-1 and 2 (Dc3 promoter-binding factor-1 and 2) binding core sequence; Found in the carrot (D.c.) Dc3 gene promoter; Dc3 expression is normally embryo-specific, and also can be induced by ABA. |
| 53 | LTRECOREAT COR15 | 663(+) | CCGAC | Core of low temperature responsive element (LTRE) of cor15a gene in Arabidopsis/A portion of repeat-C (C-repeat), TGGCCGAC, which is repeated twice in cor15a promoter. |
| 54 | MYBPLANT | 706(+) | MACCWAMC | Plant MYB binding site |
| 55 | CCA1ATLHCB1 | 740(+) | AAMAATCT | CCA1 binding site; CCA1 protein (myb-related transcription factor. interact with two imperfect repeats of AAMAATCT in Lhcb1*3 gene of Arabidopsis thaliana Related to regulation by phytochrome. |

Example 8

Deletion Construct Transformation in Model Crops

In order to ascertain the activity of the two deletion constructs, pMDCΔ1, and pMDCΔ2, as described in detail elsewhere in the instant disclosure, pMDC p2Δ1-1, pMDC p2Δ2-1 positive transformants were obtained and confirmed by PCR as well as histochemical GUS assays in both Arabidopsis (FIG. 6A, B), and rice (FIG. 16).

Quantification of GUS activity in transformed rice leaf samples (FIG. 16) reveal that promoter activity of p2Δ1 or p2Δ2 is about 2-3 fold lower than that of the full promoter p2 (FIG. 14, and FIG. 15). Table 8, and Table 9 below provides the results as graphically depicted in FIG. 14, and FIG. 15 respectively.

TABLE 8

| | MUG Assay result | | | |
|---|---|---|---|---|
| Plant code | pMOI MU/µg protein/min | pMOI MU/µg protein/min | Average | SE |
| EP control | 1.69 | 3.9 | 2.795 | 1.105 |
| CaMV35S | 25153.37 | 30980.18 | 28066.775 | 2913.405 |
| p2Δ1-Exp.2-8B | 987.76 | 1310.55 | 1149.155 | 161.395 |
| p2Δ1-Exp.1-7B | 694.69 | 948.23 | 821.46 | 126.77 |
| p2Δ2-Exp.1-5A | 581.49 | 790.14 | 685.815 | 104.325 |

TABLE 8-continued

| | MUG Assay result | | | |
|---|---|---|---|---|
| Plant code | pMOI MU/μg protein/ min | pMOI MU/μg protein/ min | Average | SE |
| p2Δ2-Exp.1-6B | 3159.02 | 4307.244783 | 3733.132392 | 574.1123915 |
| p2-8B-7-4 | 1607.4 | 2147.694913 | 1877.547456 | 270.1474565 |
| p2-8A-15-9 | 3279.52 | 4287.926852 | 3783.723426 | 504.203426 |

TABLE 9

| | MUG assay result | | | |
|---|---|---|---|---|
| Plant code | pMOI MU/μg protein/min | pMOI MU/μg protein/min | Average | SE |
| EP control | 1324.06 | 2251.2 | 1787.63 | 463.57 |
| CaMV35S-T1 plant | 63433.07 | 82376.78 | 72904.925 | 9471.855 |
| p2Δ1-Exp.2-8B | 5772.9 | 8100.87 | 6936.885 | 1163.985 |
| p2Δ1-Exp.1-7B | 21325.24 | 29711.92 | 25518.58 | 4193.34 |
| p2Δ2-Exp.1-5A | 8335 | 10869.04 | 9602.02 | 1267.02 |
| p2Δ2-Exp.1-6B | 5848.89 | 7890.37 | 6869.63 | 1020.74 |
| p2-8B-7-4 | 3577.43 | 4915.02 | 4246.225 | 668.795 |
| p2-8A-15-9 | 59131.81 | 81472.72 | 70302.265 | 11170.455 |

These data as discussed above suggest that the full promoter p2 likely comprises sequences upstream of the deletion constructs, which aid in expression of a gene of interest operably linked to the said promoter.

Example 9

Promoter p2 Activity Under Stress Conditions

Once it was determined that the p2 promoter, and deletion constructs can drive expression of a gene of interest, GUS in this case, it was examined if the promoter exhibits any differential activity in the presence of stressors such as salt, water, or temperature (heat/cold).

In two different transgenic *Arabidopsis* plants harbouring the p2 promoter operably linked to GUS, flowering stage plants (48 days old), or rice transgenics were subjected to 150 mM salt (NaCl) stress for 2 hours and 5 hours respectively. As seen in FIG. 9, in transgenic *Arabidopsis*, there is a gradual 1-2 fold increase in GUS expression upon exposure to salt stress. FIG. 10 shows the qualitative histochemical GUS staining in *Arabidopsis* whole plants upon salt stress. In transgenic rice plants, it can be seen from FIG. 11, and FIG. 12 that there is about a 1.3 fold increase in GUS expression with time.

Transgenic *Arabidopsis* harbouring the p2 promoter were also subjected to water stress by withholding 45 day old plants from water. Contrary to the results obtained in salt stress, it was observed that water stress leads to reduction in GUS levels in leaves sampled after 3, and 11 days (FIG. 13), whereby expression is limited to roots only.

Transgenic rice plants harbouring the p2 promoter were exposed to cold temperature stress (4° C. for 2 hours). No change in GUS expression was observed. The plants were separately also exposed to heat stress (42° C. for 4 hours). Similar to cold stress, even in heat stress, no change in GUS expression levels were observed.

Overall, these data provide a novel promoter from cotton, which shows constitutive activity across various tissue types. Further, this promoter is functional in other plants also, such as rice, and *Arabidopsis*. Further, the promoter also shows differential response to salt stress, and water stress, but is not affected by temperature. Deletion analysis of the construct reveals that there are elements in the promoter which are involved in enhancing the promoter activity. Characterization of the said promoter allows for use of the promoter for generating transgenic plants with heterologous expression of any operably linked gene of interest, whose expression may be in a pan tissue matter, or particularly in roots in response to water stress.

We claim:

1. A DNA construct comprising a promoter capable of driving expression of an operably linked heterologous gene of interest, said promoter selected from the group consisting of:
   a. a DNA having the sequence as set forth in SEQ ID NO: 1; and
   b. a DNA having the DNA sequence as set forth in SEQ ID NO: 1, SEQ ID NO: 9 or SEQ ID NO: 10, wherein said promoter is operably linked to a heterologous gene fragment.

2. A DNA vector comprising the DNA construct as claimed in claim 1.

3. A recombinant host cell comprising the DNA construct as claimed in claim 1, wherein said host cell is of bacterial, fungal, or plant origin.

4. A recombinant host cell comprising the DNA vector as claimed in claim 2, wherein said host cell is of bacterial or fungal origin.

5. A transgenic plant or part thereof, including seeds, comprising within its genome, a DNA construct comprising a promoter capable of driving expression of an operably linked heterologous gene of interest, said promoter selected from the group consisting of:
- a) a DNA having the sequence as set forth in SEQ ID NO: 1; and
- b) a DNA having the DNA sequence as set forth in SEQ ID NO: 1, SEQ ID NO: 9 or SEQ ID NO: 10, wherein said promoter is operably linked to a heterologous gene fragment.

6. The transgenic plant as claimed in claim 5, wherein said plant is a monocot, or a dicot.

7. A method of producing a transgenic plant, said method comprising:
- a) obtaining plant cell;
- b) obtaining a DNA construct comprising a promoter operably linked to a heterologous gene of interest, said promoter selected from the group consisting of:
  - (i) a DNA having the sequence as set forth in SEQ ID NO:1; and
  - (ii) a DNA having the DNA sequence as set forth in SEQ ID NO: 1, SEQ ID NO: 9 or SEQ ID NO: 10;
- (c) transforming said plant cell with said DNA construct of step (b), to obtain a transformed plant cell; and
- (d) selecting the transformed plant cell expressing said gene of interest.

8. The method as claimed in claim 7, wherein said gene of interest expression is constitutive.

9. The method as claimed in claim 7, wherein said gene of interest expression is regulated in response to salt or water stress.

10. The method as claimed in claim 7, wherein said gene of interest expression is root specific under conditions of water stress.

11. The method as claimed in claim 7, wherein said transformation is carried out by a method selected from the group consisting of particle gun bombardment method, microinjection method, and macroinjection method.

12. A method of generating a transgenic plant, said method comprising:
- (a) obtaining plant cell;
- (b) obtaining a DNA construct comprising a promoter operably linked to a heterologous gene of interest, said promoter selected from the group consisting of:
  - (i) a DNA having the sequence as set forth in SEQ ID NO: 1; and
  - (ii) a DNA having the DNA sequence as set forth in SEQ ID NO: 1, SEQ ID NO: 9 or SEQ ID NO: 10,
- (c) transforming a host cell with the DNA construct of step (b) to obtain a recombinant host cell;
- (d) transforming said plant cell with said recombinant host cell of step (c) to obtain a transformed plant cell; and
- (e) selecting the transformed plant cell expressing said gene of interest.

13. The method as claimed in claim 12, wherein said gene of interest expression is constitutive.

14. The method as claimed in claim 12, wherein said gene of interest expression is regulated in response to salt or water stress.

15. The method as claimed in claim 12, wherein said gene of interest expression is root specific under conditions of water stress.

16. The method as claimed in claim 12, wherein said transformation is carried out by a method selected from the group consisting of an *Agrobacterium*-mediated transformation method, and an in-planta transformation method.

* * * * *

SEQUENCE LISTING

```
<160> NUMBER OF SEQ ID NOS: 13

<210> SEQ ID NO 1
<211> LENGTH: 1956
<212> TYPE: DNA
<213> ORGANISM: artificial sequence
<220> FEATURE:
<223> OTHER INFORMATION: 1956bp long nucleotide sequence of constitutive
      plant promoter ("p2") from cotton

<400> SEQUENCE: 1
tgaccaactt tcccctaagg tacgagactt tctaaagtct ctcatttcca gaccctctaa      60
agccaatttt gacctattgc tttgactctt catttttctt gaaatactaa tgtctgatac     120
actcatgtct aatataggta tagggatata accttcccag aatcctccaa atatatagga     180
aaatatagaa aaaaatttga acatcccctt gtcagatact atgctccttg gacctgggtg     240
tagtgtagtg taaggtatgg gtatagttag atatttcttt taagtttttt catgtatttg     300
gagaatcttt tgatgtcaga tatccatatc catgtctcag acacaagtgg tgaacatggt     360
atttcaacaa aaatgaagtg tcgcaacaac attggtcgga tatatattgg tatctgacac     420
tcatggatga gttagagttg acatgtttta aagattatgg gtttcacatt acagacggag     480
ctttgctctc ttttcttggt tgatgctaaa ttggtattgt ggttattgcg ctaaagttaa     540
```

```
gatggtcggt ttgaatgatg tacaggcatg tgatattaaa gacccaaagc aaaacataga       600
gtggacagtg ccagaaggag gaggtggccc aggctattca gtcatgtaga atatataagc       660 taatccccctt tcttatcatt gctcgttgca aatatagttc tactttttgta ctttacaaca     720 aatacattat ctttgaaata attggtaagt cccatcttaa ttgctacaaa aatttaactt       780
tttactatac caaatgaaaa gaaagcttta aggagttcat gaaagttcat aatcttgagt       840 cttaccctg gatttgcctt caatctcaag taatcaaggt tttccattta ataactgat         900 tgttaacgag tcaatatgac atagaagtct agctagtttc tcaaggcaat ccagaatggt       960
aagcagctgt tagaaatgtt tcgaatcaag cggtggcctc aacaggact aaggttaaag       1020 gtttatacca gaaaacctca aaatccaaca tcctccctct tatctgcgga ttgtggataa      1080
agatgggtca cctgctctac gctattttat tgatgaatat actttgtttt cttctgcttt      1140
tatgttaatc atagttgttt actttgttag tgaataaact ggttatcatg cagaggaaca      1200
aaaaagaaaa ggataattat atagctgaaa cctaatgacg tgtagtctgt taatagacca      1260
ctaataatta atattttcaa tctttgataa catcaaataa aaataccatt tattccttat      1320
ctataaaaaa ggacacatta tcattatcac ttacatgtga aattataata aacttttta       1380 cgtaatattt tagcaaatct tacagcattt ttgattggat ttatttaagt atggtatata      1440
ttaataaata tttaaccgat aattataaaa ttttaaatat taatttactt taaatttgac     1500
atgtattatc tatattaatg taccataaaa taggatgcta aaatattaat agtataaatt      1560
ataaagcgta ttttacatca atataactag atatttactt aaataattat ttgattaaaa     1620
tttaacaacg tatccattat atatggtcat aattgtagaa agaataaata accattgcaa      1680
ttgaatattg caaagatga ttgaaaatgt atgtggtgtc atagtgatga gatacgttga      1740
taatgggatt ggattaggac atccaaaaga aaagcttctt tgatttgcca caagttcaca      1800
tcccgtgaga ctacagtttg gttgaacaat aatctcaaca cccgacagga cccaaagcaa     1860
attcagggtt cacggactac tctccaccaa acttttctcc attcattcct ctataaataa     1920
caatctctgg gtagcttgcc acatcataaa aaaagt                                1956
```

<210> SEQ ID NO 2
<211> LENGTH: 39
<212> TYPE: DNA
<213> ORGANISM: artificial sequence
<220> FEATURE:
<223> OTHER INFORMATION: forward primer with PstI site and CACC site for
      generating SEQ ID NO: 1

<400> SEQUENCE: 2
cacctgcagt gaccaacttt cccctaaggt acgagactt                              39

<210> SEQ ID NO 3
<211> LENGTH: 36
<212> TYPE: DNA
<213> ORGANISM: artificial sequence
<220> FEATURE:
<223> OTHER INFORMATION: reverse primer with SacI site for generating
      SEQ ID NO: 1

<400> SEQUENCE: 3
gagctcactt tttttatgat gtggcaagct acccag                                 36

<210> SEQ ID NO 4

<400> SEQUENCE: 4

000

<210> SEQ ID NO 5
<211> LENGTH: 12
<212> TYPE: DNA
<213> ORGANISM: artificial sequence
<220> FEATURE:
<223> OTHER INFORMATION: nucleotide sequence of CARGNCAT motif
      identified in p2 promoter

<400> SEQUENCE: 5
ccataaaata gg                                                             12

<210> SEQ ID NO 6
<211> LENGTH: 9
<212> TYPE: DNA
<213> ORGANISM: artificial sequence
<220> FEATURE:
<223> OTHER INFORMATION: nucleotide sequence of CARGCW8GAT motif
      identified in p2 promoter

<400> SEQUENCE: 6 ataaaatag                                                                  9

<210> SEQ ID NO 7
<211> LENGTH: 10
<212> TYPE: DNA
<213> ORGANISM: artificial sequence
<220> FEATURE:
<223> OTHER INFORMATION: nucleotide sequence of CIACADIANLELHC motif
      identified in p2 promoter

<400> SEQUENCE: 7
caaggcaatc                                                                10

<210> SEQ ID NO 8
<211> LENGTH: 24
<212> TYPE: DNA
<213> ORGANISM: artificial sequence
<220> FEATURE:
<223> OTHER INFORMATION: nucleotide sequence of PRECONSCRHSP70A motif
      identified in p2 promoter

<400> SEQUENCE: 8
ccgataatta taaatttta aata                                                 24

<210> SEQ ID NO 9
<211> LENGTH: 156
<212> TYPE: DNA
<213> ORGANISM: artificial sequence
<220> FEATURE:
<223> OTHER INFORMATION: deletion fragment p2?1 of p2 promoter

<400> SEQUENCE: 9
tcccgtgaga ctacagtttg gttgaacaat aatctcaaca cccgacagga cccaaagcaa         60
attcagggtt cacggactac tctccaccaa acttttctcc attcattcct ctataaataa        120
caatctctgg gtagcttgcc acatcataaa aaaagt                                  156

<210> SEQ ID NO 10
<211> LENGTH: 777
<212> TYPE: DNA
<213> ORGANISM: artificial sequence
<220> FEATURE:
<223> OTHER INFORMATION: deletion fragment p22 of p2 promoter

```
<400> SEQUENCE: 10
tggttatcat gcagaggaac aaaaaagaaa aggataatta tatagctgaa acctaatgac      60
gtgtagtctg ttaatagacc actaataatt aatattttca atctttgata acatcaaata     120
aaaataccat ttattcctta tctataaaaa aggacacatt atcattatca cttacatgtg     180
aaattataat aaactttttt acgtaatatt ttagcaaatc ttacagcatt tttgattgga     240
tttatttaag tatggtatat attaataaat atttaaccga taattataaa attttaaata     300
ttaatttact ttaaatttga catgtattat ctatattaat gtaccataaa ataggatgct     360
aaaatattaa tagtataaat tataaagcgt atttttacatc aatataacta gatatttact    420
taaataatta tttgattaaa atttaacaac gtatccatta tatatggtca taattgtaga    480
aagaataaat aaccattgca attgaatatt gcaaaagatg attgaaaatg tatgtggtgt    540
catagtgatg agatacgttg ataatgggat tggattagga catccaaaag aaaagcttct    600
ttgatttgcc acaagttcac atcccgtgag actacagttt ggttgaacaa taatctcaac    660
acccgacagg acccaaagca aattcagggt tcacggacta ctctccacca aacttttctc    720
cattcattcc tctataaata acaatctctg ggtagcttgc cacatcataa aaaaagt      777

<210> SEQ ID NO 11
<211> LENGTH: 21
<212> TYPE: DNA
<213> ORGANISM: artificial sequence
<220> FEATURE:
<223> OTHER INFORMATION: forward primer sequence to amplify SEQ ID NO: 9

<400> SEQUENCE: 11
tcccgtgaga ctacagtttg g                                               21

<210> SEQ ID NO 12
<211> LENGTH: 27
<212> TYPE: DNA
<213> ORGANISM: artificial sequence
<220> FEATURE:
<223> OTHER INFORMATION: depicts reverse primer sequence to amplify SEQ
      ID NO: 9 or SEQ ID NO: 10

<400> SEQUENCE: 12
ggtagcttgc cacatcataa aaaaagt                                         27

<210> SEQ ID NO 13
<211> LENGTH: 19
<212> TYPE: DNA
<213> ORGANISM: artificial sequence
<220> FEATURE:
<223> OTHER INFORMATION: forward primer sequence to amplify SEQ ID NO:
      10

<400> SEQUENCE: 13
tggttatcat gcagaggaa                                                  19
```